United States Patent
Wallace et al.

(10) Patent No.: US 7,666,907 B2
(45) Date of Patent: Feb. 23, 2010

(54) SALTS OF TRIMEBUTINE AND N-DESMETHYL TRIMEBUTINE

(75) Inventors: John Wallace, Cochrane (CA); Giuseppe Cirino, Naples (IT); Vincenzo Santagada, Cosenza (IT); Giuseppe Caliendo, Napoli (IT)

(73) Assignee: Antibe Therapeutics Inc., Calgary (CA)

( * ) Notice: Subject to any disclaimer, the term of this patent is extended or adjusted under 35 U.S.C. 154(b) by 6 days.

(21) Appl. No.: 11/759,154

(22) Filed: Jun. 6, 2007

(65) Prior Publication Data

US 2007/0275905 A1 Nov. 29, 2007

Related U.S. Application Data

(63) Continuation-in-part of application No. PCT/CA2006/000484, filed on Mar. 31, 2006.

(60) Provisional application No. 60/804,067, filed on Jun. 6, 2006.

(51) Int. Cl.
*A01N 37/44* (2006.01)
*C07C 279/00* (2006.01)

(52) U.S. Cl. .................. 514/540; 514/18; 562/560

(58) Field of Classification Search .............. 514/18, 514/540, 282, 534; 560/55; 562/560
See application file for complete search history.

(56) References Cited

U.S. PATENT DOCUMENTS

| | | | |
|---|---|---|---|
| 4,301,163 A | 11/1981 | Torossian et al. | |
| 4,412,992 A | 11/1983 | Chan | |
| 4,440,763 A | 4/1984 | Lover | |
| 4,751,221 A | 6/1988 | Watanabe et al. | |
| 5,013,727 A | 5/1991 | Halskov | |
| 5,245,080 A | 9/1993 | Aubard et al. | |
| 5,541,170 A | 7/1996 | Rhodes et al. | |
| 5,811,547 A | 9/1998 | Nakamichi et al. | |
| 6,197,341 B1 | 3/2001 | Friess et al. | |
| 6,353,024 B1 * | 3/2002 | Grouhel et al. | 514/534 |
| 6,458,776 B1 | 10/2002 | Ekwuribe et al. | |
| 6,602,915 B2 | 8/2003 | Uhrich et al. | |
| 6,986,901 B2 | 1/2006 | Meisel et al. | |
| 7,041,704 B2 | 5/2006 | Burgard et al. | |
| 2002/0165276 A1 | 11/2002 | Brunelle et al. | |
| 2003/0119903 A1 | 6/2003 | Grouhel et al. | |

FOREIGN PATENT DOCUMENTS

| CA | 2204747 | 3/1997 |
|---|---|---|
| EP | 1645288 | 4/2006 |

(Continued)

OTHER PUBLICATIONS

Berge, S.M. et al., Pharmaceutical Salts, 1977, Journal of Pharmaceutical Sciences, vol. 66, No. 1, pp. 1-19.*

(Continued)

*Primary Examiner*—Rosalynd Keys
*Assistant Examiner*—Yaté K Cutliff
(74) *Attorney, Agent, or Firm*—Bennett Jones LLP

(57) ABSTRACT

Unique salts of trimebutine and N-monodesmethyl trimebutine, and their corresponding stereoisomers, having improved analgesic properties useful in the treatment of visceral pain are provided. The salts of the present invention are particularly useful in the treatment of conditions characterized by abdominal pain, such as inflammatory bowel disease (IBD) and irritable bowel syndrome (IBS), diabetic gastroparesis, and dyspepsia.

10 Claims, 8 Drawing Sheets

FOREIGN PATENT DOCUMENTS

| | | |
|---|---|---|
| WO | WO 98/48826 | 11/1998 |
| WO | WO 2004/006902 | 1/2004 |

OTHER PUBLICATIONS

Pellicciari, et al., Brush-Border-Enzyme-Mediated Intestine-Specific Drug Delivery. Amino acid Prodrugs of 5-Aminosalicylic acid, J. Med. Chem. 1993, vol. 36, pp. 4201-4207.

Dzierzewicz, et al., Susceptibility of Desulfovibrio desulfuricans intestinal strains to sulfasalazine and its biotransformation products, Med. Sci. Monit., 2004, vol. 10, No. 6, BR185-190.

Edmond, et al., The effect of 5-aminosalicylic acid-containing drugs on sulfide production by sulfate-reducing bacteria and amino acid-fermenting bacteria, Inflammatory Bowel Diseases, 2003, vol. 9, No. 1, pp. 10-17.

Fiorucci, et al., Inhibition of Hydrogen Sulfide Generation Contributes to gastric injury caused by anti-inflammatory nonsteroidal drugs, Gastroenterology, Oct. 2005, vol. 129, No. 4, pp. 1210-1224.

Distrutti, et al., Evidence that Hydrogen Sulfide exerts Antinociceptive Effects in the Gastrointestinal Tract by Activating KATP Channels, J. Pharmacology & Exp. Ther., Web Release on Sep. 25, 2005, vol. 316, No. 1, pp. 325-335.

Sidhu, et al., L-Cystein and Sodium Hydrogensulfide Inhibit Spontaneous Contractibility in Isolated Pregnant Rat Uterine Strips In Vivo, Pharmacology & Toxicology, 2001, vol. 88, pp. 198-203.

Zhao, et al., The vasorelaxant effect of H2S as a novel endogenous gaseous KATP channel opener, EMBO Journal, 2001, vol. 20, No. 21, pp. 6008-6016.

Zhao, et al., H2S-induced vasorelaxation and underlying cellular and molecular mechanisms, A. J. Physiol. Heart Circ. Physiol., 2002, vol. 283: H474-480.

Teague, et al., "The Smooth Muscle Relaxant Effect of Hydrogen Sulfide In Vitro: Evidence for a Physiological Role to Control Intestinal Contractility", Br. J. Pharmacol, vol. 137, pp. 139-145.

Abe, et al., "The possible role of hydrogen sulfide as an endogenous neuromodulator", The Journal of Neuroscience, 1996, vol. 16, No. 3, pp. 1066-1071.

Carceller, et al., "Novel Azo derivatives as prodrugs of 5-aminosalicylic acid and amino derivatives with potent platelet activating factor antagonist activity", J. Med. Chem., 2001, Vol. 44, No. 18, pp. 3001-3013.

Roman, Francois, J. et al., Pharmacological Properties of Trimebutine and N-Monodesmethyltrimebutine, The Journal of Pharmacology and Experimental Therapeutics, vol. 289, No. 3., 1391-1396.

Fornai, Matteo, et al., Differential role of cycooxygenase 1 and 2 isoforms in the modulation of colonic neuromuscular function in experimental inflammation, American Society for Pharmacology and Experimental Therapeutics, Feb. 1, 2006, JPET#98350.

Salvemini, D. et al., Endogenous Nitric Oxide Enhances Prostaglandin Production in a Model of Renal Inflammation, J. Clin. Invest vol. 93, May 1994, 1940-1947.

Uchiyama, Masanori et al., Effects of Trimebutine on Intestinal Motility after Massive Small Bowel Resection, J. Smooth Muscle Res. (2000) 36, 117-126.

Ghidini et al (1986) Single drug treatment for irritable colon: Rociverine versus trimebutine maleate. Curr Ther Res 39: 541-548.

Gauthier et al (1994) Nitric oxide attenuates leukocyte-endothelial interaction via P-selectin in splanchnic ischemiareperfusion. Am J Physiol 267: G562-G568.

Walford and Loscalzo (2003) Nitric oxide in vascular biology. J Thromb Haemost 1:2112-2118.

Kayser, V. et al., Antinociceptive effect of (S)-N-desmethyl trimebutine against a mechanical stimulus in a rat model of peripheral neuropathy, Life Sci. 2000:66(5):433-9.

\* cited by examiner

SALTS OF TRIMEBUTINE AND N-DESMETHYL TRIMEBUTINE

This application is filed as a Continuation-in-Part of PCT/CA2006/000484, filed Mar. 31, 2006, which claims priority to PCT/CA2005/000819, filed May 27, 2005. This application further claims priority to U.S. provisional patent application No. 60/804,067, filed Jun. 6, 2006.

FIELD OF INVENTION

The present invention relates to unique salts of trimebutine and N-monodesmethyl trimebutine, and their corresponding stereoisomers, having improved analgesic properties useful in the treatment of visceral pain in general and more particularly in the treatment of conditions characterized by abdominal pain, for example, in patients with intestinal diseases such as inflammatory bowel disease (IBD) and irritable bowel syndrome (IBS), diabetic gastroparesis, and dyspepsia.

BACKGROUND OF THE INVENTION

Trimebutine [3,4,5-trimethoxybenzoic acid 2-(dimethylamino)-2-phenylbutylester and its maleate salt] has been used in many countries since 1969 for the treatment of functional bowel disorders, including IBS. The efficacy of trimebutine to relieve abdominal pain has been demonstrated in various clinical studies (see, for example, Ghidini et al (1986) Single drug treatment for irritable colon: Rociverine versus trimebutine maleate. *Curr Ther Res* 39: 541-548). Trimebutine has proved to be effective in the treatment of both acute and chronic abdominal pain in patients with functional bowel disorders, especially IBS, at doses ranging from 300 to 600 mg/day. It is also effective in children presenting with abdominal pain.

It is thought that the actions of trimebutine on the gastrointestinal tract are mediated in part via (i) an agonist effect on peripheral mu, kappa and delta opiate receptors and (ii) release of gastrointestinal peptides such as motilin and modulation of the release of other peptides, including vasoactive intestinal peptide, gastrin and glucagon. Further, trimebutine accelerates gastric emptying, induces premature phase III of the migrating motor complex in the intestine and modulates the contractile activity of the colon. Recently, trimebutine has also been shown to decrease reflexes induced by distension of the gut lumen in animals to modulate visceral sensitivity.

Nitric oxide (NO) been recently been shown to exert many anti-inflammatory effects, including reduction of leukocyte adherence to the vascular endothelium (Gauthier et al (1994) Nitric oxide attenuates leukocyte-endothelial interaction via P-selectin in splanchnic ischemia-reperfusion. *Am J Physiol* 267: G562-G568) and suppression of production of various chemotactic factors (Walford and Loscalzo (2003) Nitric oxide in vascular biology. *J Thromb Haemost* 1: 2112-2118). Further, incorporation of an NO-releasing moiety into certain drugs such as NSAIDs, acetaminophen and ursodexycholic acid has been shown to enhance activities of these drugs and reduce toxicity relative to the parent drug.

Hydrogen sulfide ($H_2S$) is another type of gaseous mediator that may exert anti-inflammatory effects Recently it has been shown that $H_2S$ releasing agents exhibit analgesic activity in models of visceral pain (Distrutti et al (2005) Evidence that hydrogen sulfide exerts antinociceptive effects in the gastrointestinal tract by activating $K_{ATP}$ channels. *J Pharmacol Exp Ther* 316: 325-335. Further, $H_2S$ has been shown to be a smooth muscle relaxant in intestinal tissues (see Teague, B. et al. (2002) The Smooth Muscle Relaxant effect of Hydrogen Sulfide In Vitro: Evidence for a Physiological Role to Control Intestinal Contractility. *Br. J. Pharmacol.* 137: 139-145.

The inventors have shown in the present application that the activity of trimebutine is significantly enhanced when salts of trimebutine or N-monodesmethyl trimebutine and their corresponding stereoisomers are formed with various NO-releasing, $H_2S$-releasing or combined NO— and $H_2S$-releasing moieties. In particular, administration of these NO-releasing, $H_2S$-releasing or combined NO— and $H_2S$-releasing salts of trimebutine and N-monodesmethyl trimebutine results in improved analgesic properties when compared to trimebutine (trimebutine maleate) or its metabolite N-monodesmethyl trimebutine alone and when compared to the NO-releasing, $H_2S$-releasing or combined NO— and $H_2S$-releasing moiety alone. These salts are particularly useful in the treatment of conditions characterized by abdominal pain such as such as irritable bowel syndrome, inflammatory bowel disease, diabetic gastroparesis, dyspepsia and the like.

SUMMARY OF THE INVENTION

In general, salts of trimebutine (TMB) and its active metabolite N-desmethyl trimebutine (Nor-TMB) and their corresponding stereoisomers, (R)-TBM, (S)-TMB, (R)-Nor-TBM and (S)-Nor-TBM, are provided, said salts being formed using NO-releasing, $H_2S$-releasing or combined NO— and $H_2S$-releasing moieties. By forming a salt with an NO-releasing, $H_2S$-releasing or combined NO— and $H_2S$-releasing moiety, the anti-nociceptive effect of TMB and Nor-TMB was surprisingly enhanced.

More particularly, the TMB and Nor-TMB salts of the present invention are superior to TMB and Nor-TMB alone and to an NO-releasing, $H_2S$-releasing or combined NO— and $H_2S$-releasing moiety alone in reducing visceral pain associated with colorectal distension. The NO-releasing, $H_2S$-releasing or combined NO— and $H_2S$-releasing moieties alone did not appear to have any significant effects on visceral pain associated with colorectal distension when administered alone. Thus, in one aspect of the invention, the salts of the present invention are useful in alleviating pain associated with any disorder of the digestive system that is associated with abdominal pain.

Broadly stated, salts of the invention have the following general formula:

$$A^+.X^- \quad \text{(formula I)}$$

where:

A is

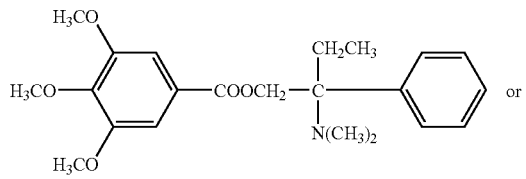

Trimebutine or

-continued

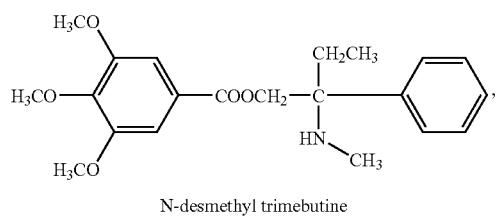
N-desmethyl trimebutine and their corresponding stereoisomers;

and X is a NO-releasing, H₂S-releasing or combined NO— and H₂S-releasing moiety.

In a preferred embodiment, X is selected from the group consisting of:

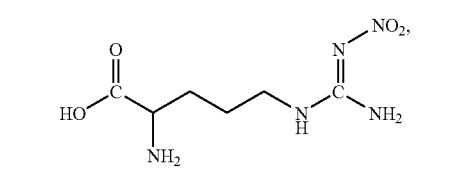
nitroarginine

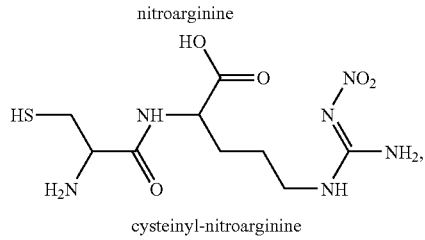
cysteinyl-nitroarginine

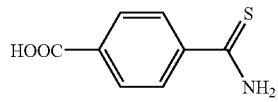
4-(thiocarbamoyl) benzoic acid

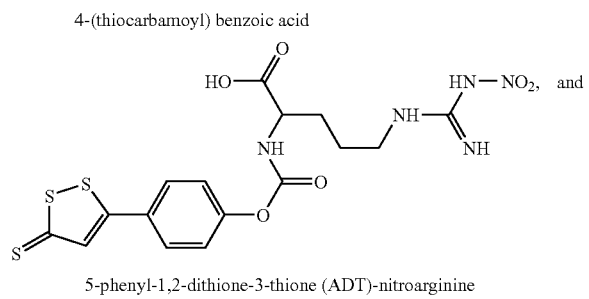
5-phenyl-1,2-dithione-3-thione (ADT)-nitroarginine

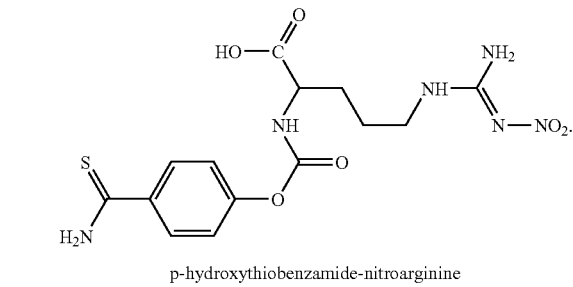
p-hydroxythiobenzamide-nitroarginine

It is understood that any non-toxic, effective NO-releasing, H₂S-releasing or combined NO— and H₂S-releasing moiety can be used in the present invention.

Preferred compounds are those of the following formulae:

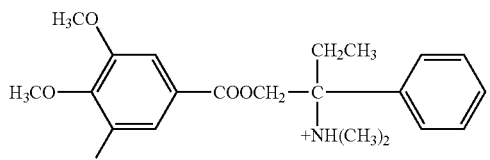
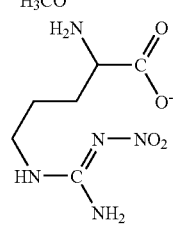
I
Trimebutine nitroargininate (I)

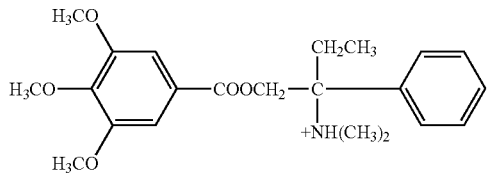
II
Trimebutine cysteinyl-nitroargininate (II)

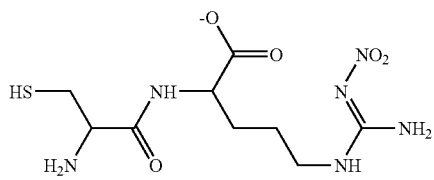
III
Trimebutine thiocarbamoylbenzoate (III)

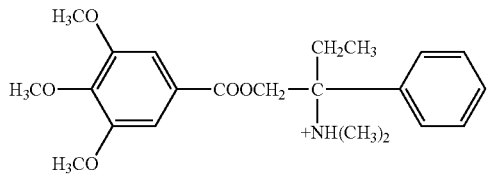
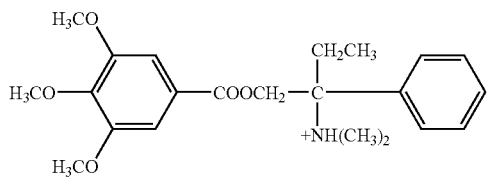
IV
Trimebutine 5-phenyl-1,2-dithione-3-thione (ADT)-nitroargininate (IV)

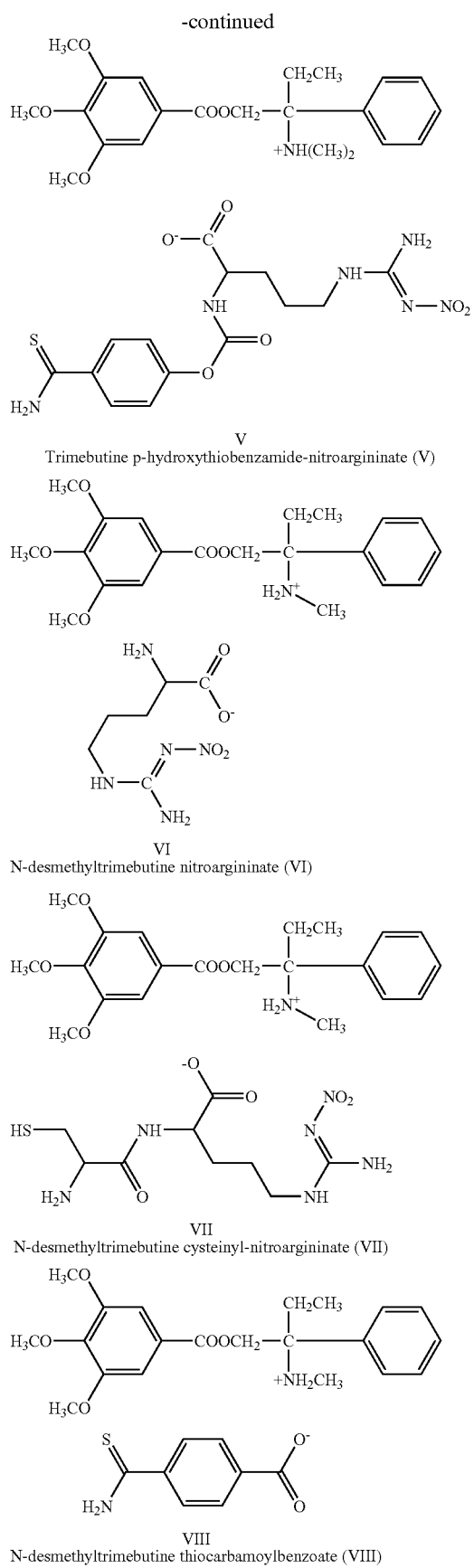
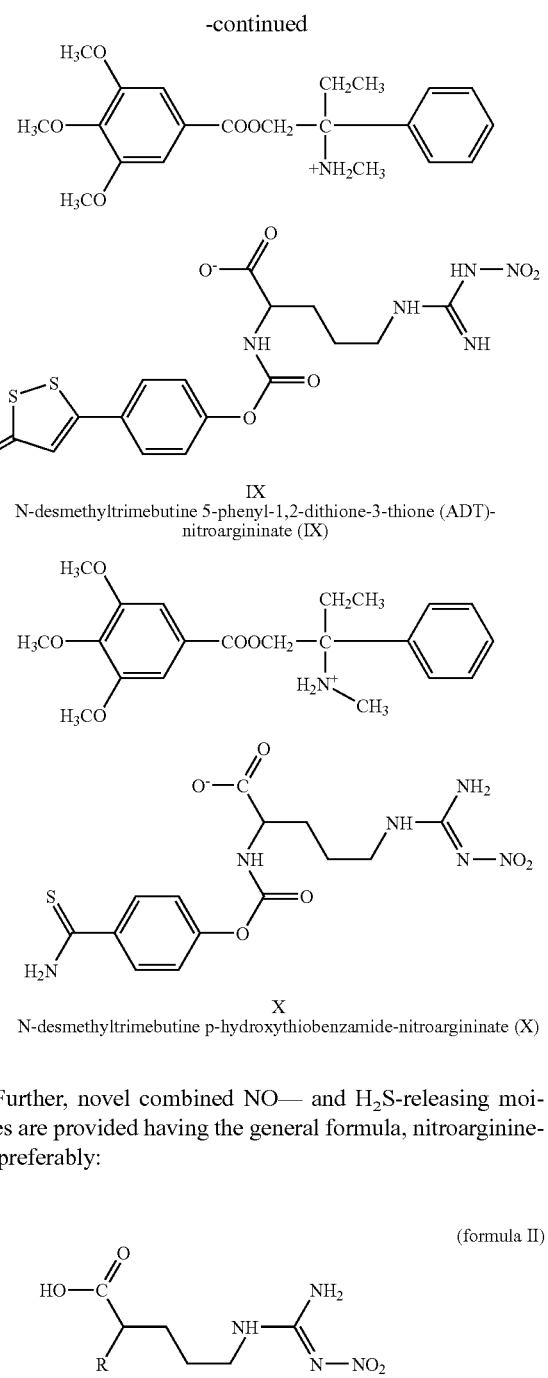

Further, novel combined NO— and H$_2$S-releasing moieties are provided having the general formula, nitroarginine-R, preferably:

$$\text{(formula II)}$$

wherein R is an H$_2$S-releasing moiety. In a preferred embodiment, R is selected from the group consisting of 5-p-hydroxyphenyl-1,2-dithione-3-thione, cysteine, and 4-(thiocarbamoyl) benzoic acid.

Further, a method for treating visceral pain in a subject in need of such treatment is provided comprising administering to the subject a visceral pain relieving amount of a compound of the present invention. In one embodiment, the visceral pain is abdominal pain. In another embodiment, the abdominal pain is due to intestinal diseases such as inflammatory bowel disease (IBD), irritable bowel syndrome (IBS), diabetic gastroparesis, and dyspepsia.

DETAILED DESCRIPTION OF THE PREFERRED EMBODIMENT

Figure 1:
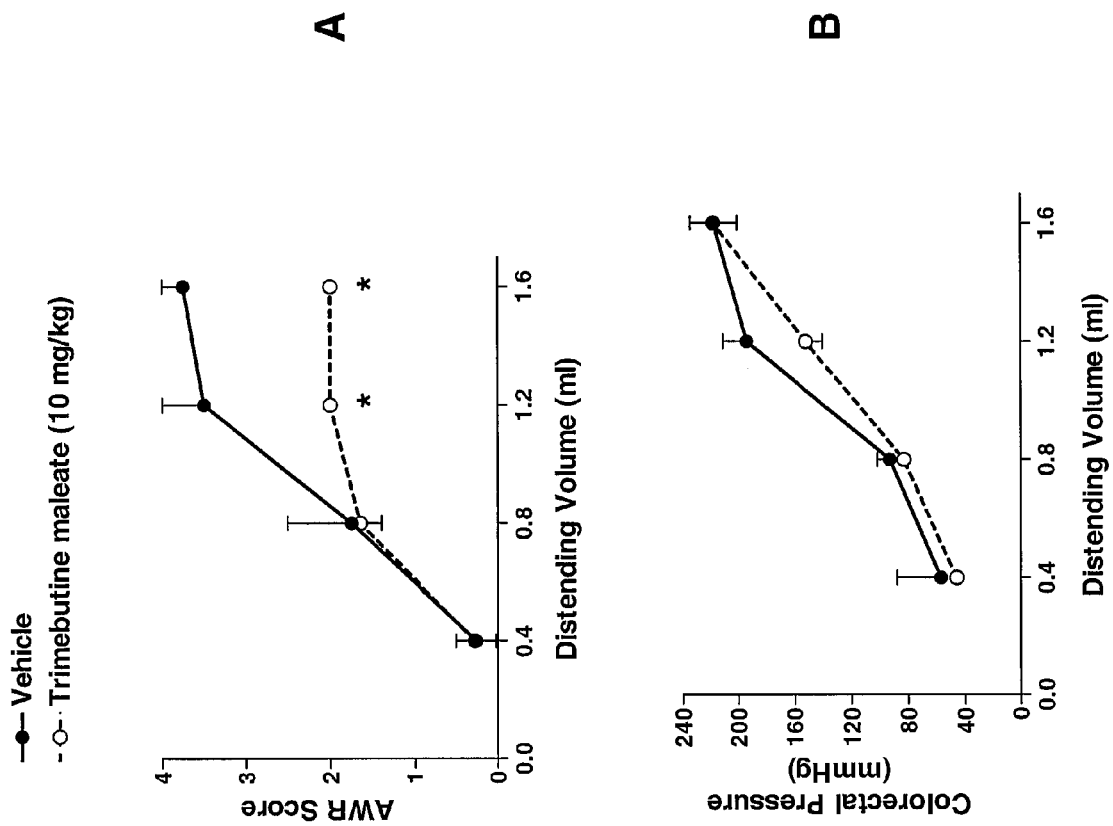
FIG. 1(a) shows the perception score (AWR Score) in a rat model of visceral pain perception using vehicle and trimebutine maleate.
FIG. 1(b) shows the colorectal pressure (mmHg) in a rat model of visceral pain perception using vehicle and trimebutine maleate alone.
Figure 2:
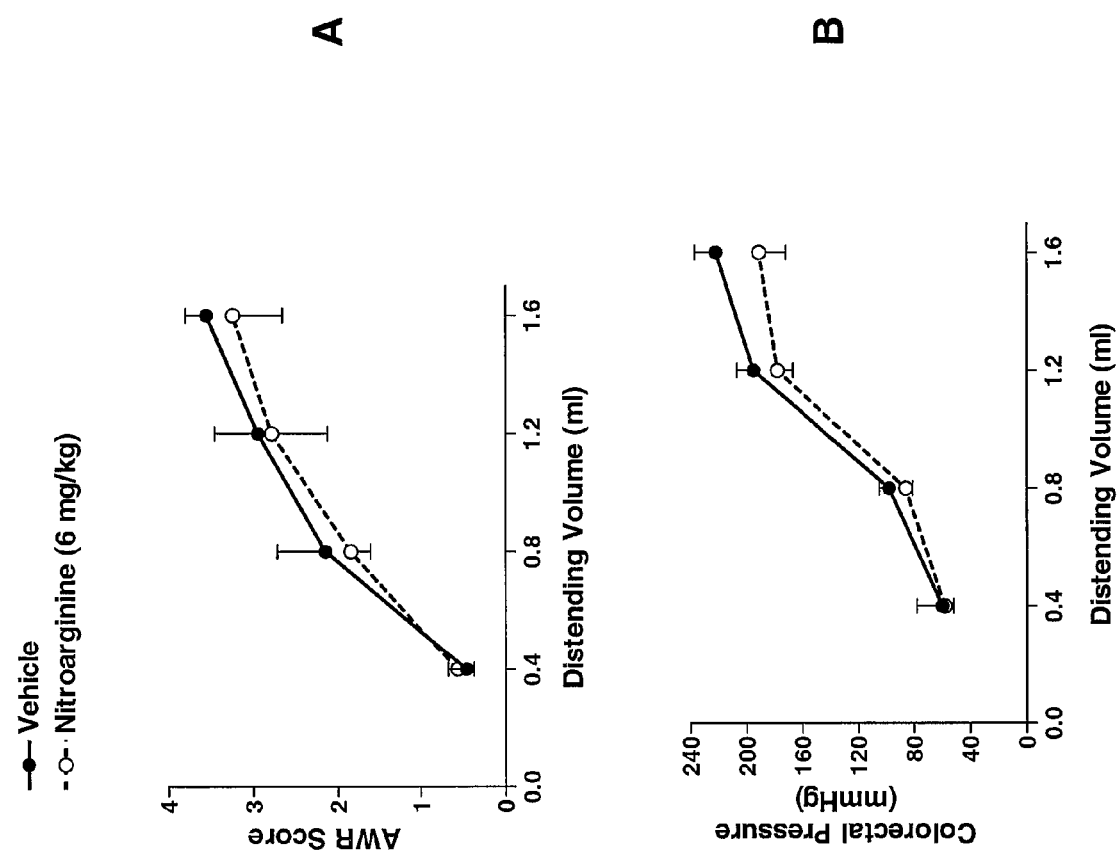
FIG. 2(a) shows the perception score (AWR Score) in a rat model of visceral pain perception using vehicle and nitroarginine alone.
FIG. 2(b) shows the colorectal pressure (mmHg) in a rat model of visceral pain perception using vehicle and nitroarginine alone.
Figure 3:
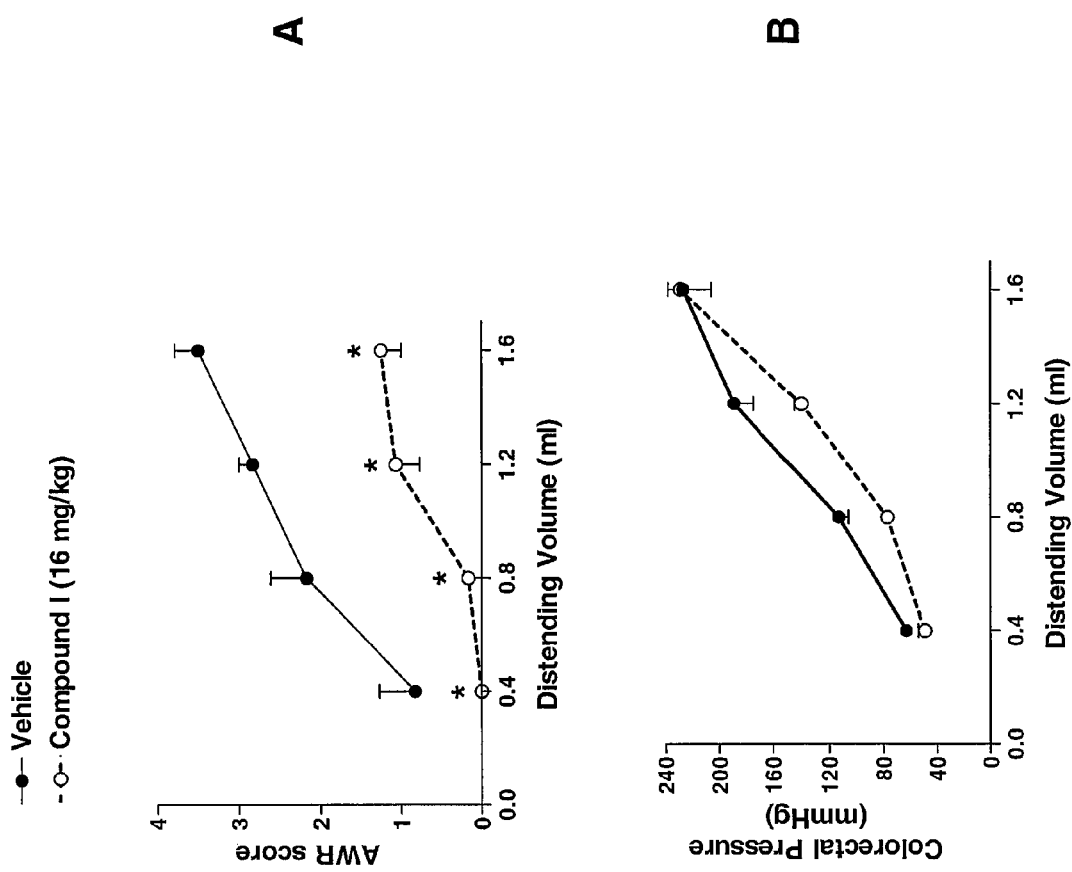
FIG. 3(a) shows the perception score (AWR Score) in a rat model of visceral pain perception using vehicle and trimebutine nitroargininate (salt I).
FIG. 3(b) shows the colorectal pressure (mmHg) in a rat model of visceral pain perception using vehicle and trimebutine nitroargininate (salt I).

The invention will now be described with respect to preferred embodiments described herein. It should be appreciated however that these embodiments are for the purpose of illustrating the invention, and are not to be construed as limiting the scope of the invention as defined by the claims.

The compounds of the present invention contain two active moieties, (1) either TMB or Nor-TMB, or their stereoisomers, and (2) an NO-releasing moiety, an $H_2S$-releasing moiety, or combined NO— and $H_2S$-releasing moieties. In many instances, the salts of the present invention can be made using known starting materials and reagents.

Compounds of the present invention may be utilized for the treatment of visceral pain, such as abdominal pain, associated with various diseases, including, but not limited to, Crohn's disease, ulcerative colitis, irritable bowel syndrome, infectious colitis (e.g., pseudomembranous colitis such as *Clostridium difficile* colitis, *salmonella enteritis, shigella* infections, yersiniosis, cryptosporidiosis, microspridial infections, and viral infections), radiation-induced colitis, colitis in the immunocompromised host, diabetic gastroparesis and dyspepsia.

Depending on the specific condition or disease state to be treated, subjects may be administered compounds of the present invention at any suitable therapeutically effective and safe dosage, as may be readily determined within the skill of the art. These compounds are, most desirably, administered in dosages ranging from about 1 to about 2000 mg per day, in a single or divided doses, although variations will necessarily occur depending upon the weight and condition of the subject being treated and the particular route of administration chosen. However, a dosage level that is in the range of about 0.1 to about 100 mg/kg, preferably between about 5 and 90 mg/kg, and more preferably between about 5 and 50 mg/kg, is most desirable. Variations may nevertheless occur depending upon the weight and conditions of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such large doses are first divided into several small doses for administration throughout the day.

The compounds of the present invention can be administered in the form of any pharmaceutical formulation, the nature of which will depend upon the route of administration. These pharmaceutical compositions can be prepared by conventional methods, using compatible, pharmaceutically acceptable excipients or vehicles. Examples of such compositions include capsules, tablets, transdermal patches, lozenges, troches, sprays, syrups, powders, granulates, gels, elixirs, suppositories, and the like, for the preparation of extemporaneous solutions, injectable preparations, rectal, nasal, ocular, vaginal etc. A preferred route of administration is the oral and rectal route.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of similar type may also be employed as fillers in gelatin capsules; preferred materials in this connection also include lactose or milk sugar, as well as high molecular weight polyethylene glycols. When aqueous suspensions and/or elixirs are desired for oral administration the active ingredient may be combined with sweetening or flavoring agents, coloring matter and, if so desired, emulsifying and/or suspending agents, together with such diluents as water, ethanol, propylene glycol, glycerin and various combinations thereof.

The dosage form can be designed for immediate release, controlled release, extended release, delayed release or targeted delayed release. The definitions of these terms are known to those skilled in the art. Furthermore, the dosage form release profile can be effected by a polymeric mixture composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

For parenteral administration, a solution of an active salt in either sesame or peanut oil or in aqueous propylene glycol can be employed. The aqueous solutions should be suitably buffered (preferably pH greater than 8), if necessary, and the liquid diluent first rendered isotonic. The aqueous solutions are suitable for intravenous injection purposes. The preparation of all these solutions under sterile conditions is readily accomplished by standard pharmaceutical techniques well known to those skilled in the art.

The following non-limitative examples further describe and enable a person ordinarily skilled in the art to make and use the invention.

Preparation of Compounds

Example 1

Synthesis of trimebutine nitroargininate (I)

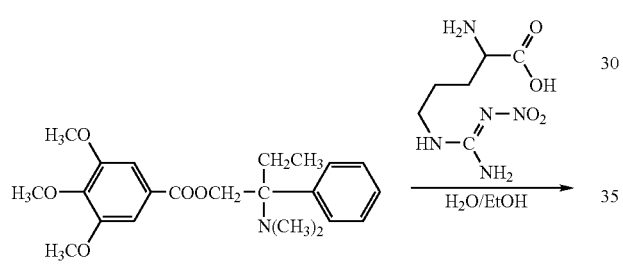
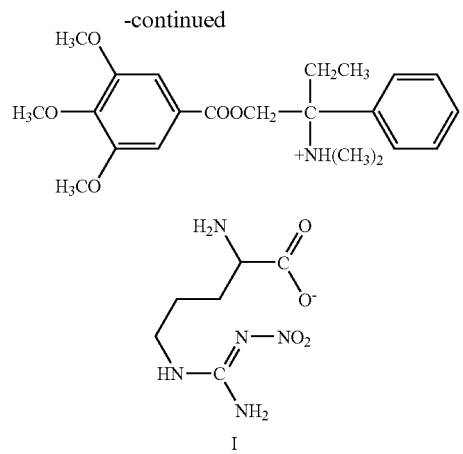

To a mixture of H-Arg(NO$_2$)—OH (0.1 mole) and trimebutine (0.1 mole), water (200 mL) and ethyl alcohol (20 mL) have been added and the resulting suspension has been stirred at room temperature until clear. Then the solution has been frozen and lyophilized furnishing the desired salt (quantitative yield).

$^1$H-NMR (400 MHz, DMSO-d$_6$): δ 0.60 (t, 3H), 1.45-1.75 (m, 4H), 1.80-1.90 (m, 2H), 2.25 (s, 6H), 2.90-3.40 (m, 2H), 3.75 (s, 9H), 3.95 (m, 1H), 4.64 (dd, 2H), 7.15 (s, 2H), 7.22 (t, 1H), 7.35 (t, 2H), 7.46 (d, 2H).

$^{13}$C-NMR (400 MHz, DMSO-d$_6$): δ 9.07, 22.8, 26.4, 28.9, 29.1, 47.9, 56.4, 60.8, 64.4, 65.8, 107.3, 125.2, 127.4, 128.0, 128.5, 141.7, 142.5, 153.4, 158.3, 165.9, 170.2.

mp 183° C. (dec).

Example 2

Synthesis of trimebutine cysteinyl-nitroargininate (II)

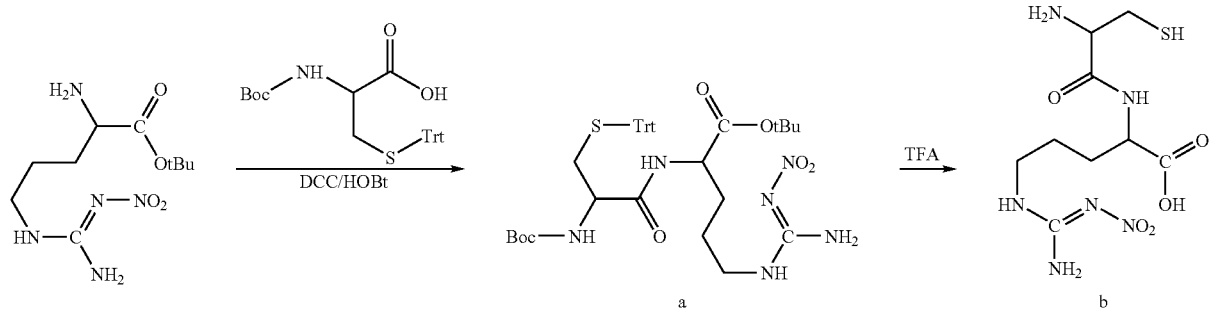
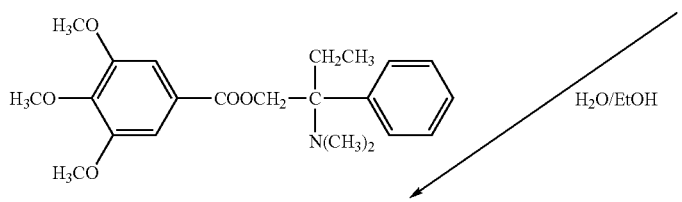

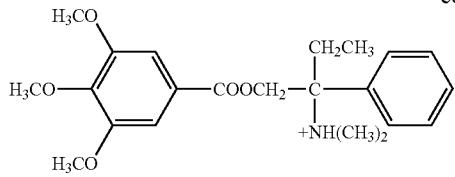

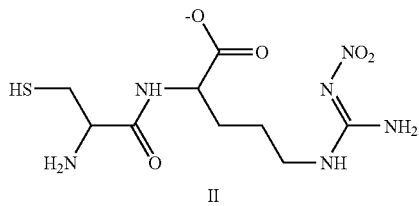

Synthesis of 2-(2-amino-3-mercapto-propionylamino)-5-nitroguanidino-pentanoic acid (b)

To a solution of Boc-Cys(Trt)-OH (3.0 mmol) in 50 mL of dimethylformamide, hydroxybenzotriazole (3.3 mmol) and DCC (3.3 mmol) were added with stirring at 0° C. for 1 h. To the reaction mixture, H-Arg(NO$_2$)-OtBu (3.0 mmol) was added and stirred mechanically for 3 h at 0° C. and 24 h at room temperature. After filtration, the filtrate was evaporated under reduced pressure to remove the solvent. The oily residue thus obtained was dissolved in ethyl acetate; the organic layer was washed with brine, dried on anhydrous MgSO$_4$, filtered and the solvent evaporated. The crude intermediate a was treated with a solution of trifluoroacetic acid in dichloromethane (40% TFA in DCM). After 1 h the solvent was removed to obtain H-Cys-Arg(NO$_2$)—OH.TFA as a crude residue which was precipitated with diethyl ether; the obtained solid was dissolved in water and 1N NaOH was slowly added to obtain 2-(2-amino-3-mercapto-propionylamino)-5-nitroguanidino-pentanoic acid (b) as a white solid which was recovered by filtration.

Synthesis of trimebutine cysteinyl-nitroargininate (II)

To a mixture of 2-(2-amino-3-mercapto-propionylamino)-5-nitroguanidino-pentanoic acid (b; 0.1 mole) and trimebutine (0.1 mole), water (200 mL) and ethyl alcohol (20 mL) have been added and the resulting suspension has been stirred at room temperature until clear. Then the solution has been frozen and lyophilized furnishing the desired salt (quantitative yield).

Example 3

Synthesis of trimebutine thiocarbamoylbenzoate (III)

Preparation of 3,4,5-trimethoxybenzoic acid 2-(dimethylamino)-2-phenylbutyl ester 4-thiocarbamoyl benzoate (Trimebutine thiocarbamoylbenzoate)

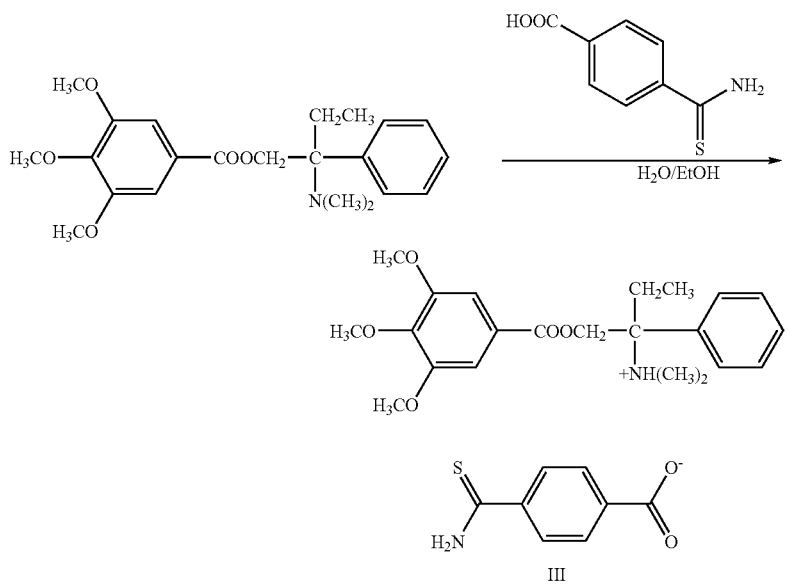

To a mixture of 4-(thiocarbamoyl) benzoic acid (0.1 mol) and trimebutine (0.1 mol), water (200 mL) and ethyl alcohol (20 mL) have been added and the resulting suspension has been stirred at room temperature until clear. Then the solution has been frozen and lyophilized furnishing the desired salt (quantitative yield).

$^1$H-NMR (400 MHz, DMSO-$d_6$): δ 0.60 (t, 3H), 1.45-1.75 (m, 4H), 1.80-1.90 (m, 2H), 2.28 (s, 6H), 2.90-3.40 (m, 2H), 3.69 (s, 9H), 3.95 (m, 1H), 4.73 (dd, 2H), 7.01 (s, 2H), 7.22 (t, 1H), 7.35 (t, 2H), 7.46 (d, 2H) 7.93 (dd, 4H), 9.65 (bs, 1H, NH), 10.05 (bs, 1H, NH).

$^{13}$C-NMR (400 MHz, DMSO-$d_6$): δ 9.07, 28.9, 56.5, 60.8, 64.5, 65.7, 107.1, 125.3, 127.4, 128.1, 128.6, 129.5, 129.7, 132.3, 141.8, 142.5, 148.5, 153.4, 154.8, 165.9, 169.4, 172.5, 188.6.

mp 66-68° C. (dec).

Synthesis of 4-(thiocarbamoyl) benzoic acid

The compound was synthesized according to a procedure already reported in literature (Fairfull, E. S., Lowe J. L., Peak D. A. *J. Chem. Soc.* 1952, 742), incorporated herein by reference.

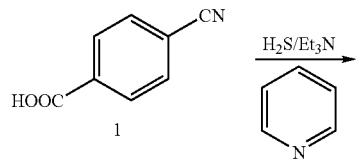

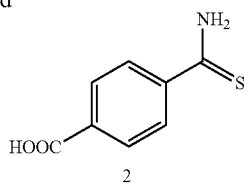

4-(Thiocarbamoyl) benzoic acid (2)

3 g of 4-cyanobenzoic acid 1 (20.4 mmol) were dissolved in 40 mL of pyridine and 2.1 mL of triethylamine (20.4 mmol) were added. Dry hydrogen sulphide was passed through the solution in a steady steam for 4 h. The mixture was then poured into water and the solid collected by filtration. Recrystallization from petroleum ether furnished 2.51 g of the pure compound 2 (68% yield).

MS (ESI), m/e 182.2 (M$^+$).

$^1$H NMR (DMSO-$d_6$): δ 7.92 (dd, 4H), 9.68 (s, 1H, NH), 10.12 (s, 1H, NH), 13.25 (s, 1H, OH).

$^{13}$C NMR (DMSO-$d_6$): δ 127.3, 129.6, 132.0, 148.5, 169.4, 188.6 m.p. 296-298° C. (dec.)

Example 4

Synthesis of trimebutine ADT-nitroargininate (IV)

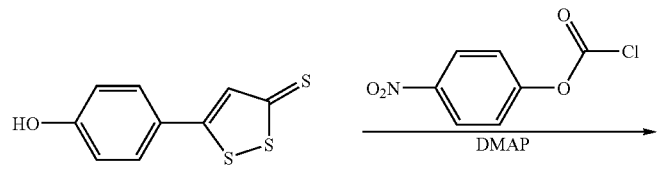

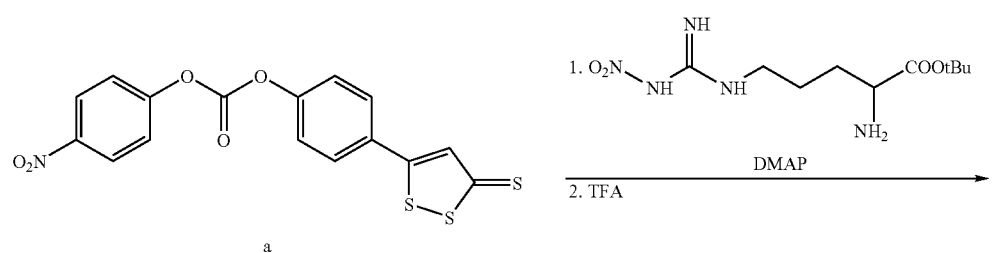

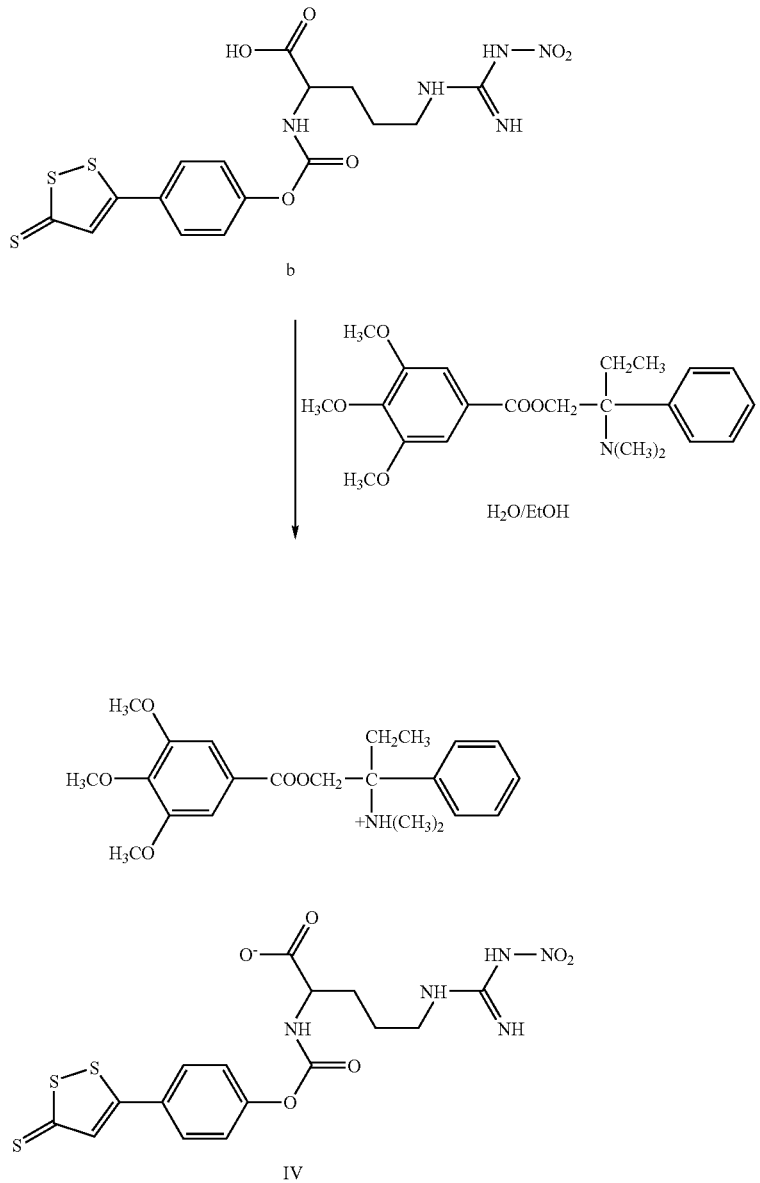

Synthesis of carbonic acid 4-nitro-phenyl ester 4-(5-thioxo-5H-[1,2]dithiol-3-yl)-phenyl ester (a)

To a stirred suspension of ADT-OH (1.04 mmol) in CH$_2$Cl$_2$ (10 ml) was added 4-dimethylaminopyridine (DMAP, 1.16 mmol) and 4-nitrophenyl chloroformate (1.15 mmol). The reaction mixture was stirred for 10 hr at room temperature. Thin layer chromatography indicated that the formation of the desired product completed. The solvent was removed and the residue was treated with diethyl ether; product a was recovered by filtration and used without further purification (yield 81%).

Synthesis of 5-nitroguanidino-2-[4-(5-thioxo-5H-[1,2]dithiol-3-yl)-phenoxycarbonyl-amino]-pentanoic acid (b)

To the solution of a (1.04 mmol) in 50 mL of CH$_2$Cl$_2$ were added 4-dimethylaminopyridine (1.16 mmol) and H-Arg(NO$_2$)-OtBu (1.02 mmol) and the solution was stirred for 20 hr at room temperature. Then, the reaction mixture was diluted with CH$_2$Cl$_2$, washed with sat. NaHCO$_3$ and sat. NaCl, and dried over MgSO$_4$. The crude intermediate was treated with a solution of trifluoroacetic acid in dichloromethane (40% TFA in DCM). After 1 h the solvent was removed to obtain product b as a crude residue which was precipitated with diethyl ether; the obtained solid was dissolved in water and 1N NaOH was slowly added to obtain 5-nitroguanidino-2-[4-(5-thioxo-5H-[1,2]dithiol-3-yl)-phenoxycarbonyl-amino]-pentanoic acid (b) as a white solid which was recovered by filtration.

Synthesis of trimebutine ADT-nitroargininate (IV)

To a mixture of 5-nitroguanidino-2-[4-(5-thioxo-5H-[1,2]dithiol-3-yl)-phenoxycarbonyl-amino]-pentanoic acid (b; 0.1 mol) and trimebutine (0.1 mol), water (200 mL) and ethyl alcohol (20 mL) have been added and the resulting suspension has been stirred at room temperature until clear. Then the solution has been frozen and lyophilized furnishing the desired salt (quantitative yield).

Example 5

Synthesis of trimebutine p-hydroxythiobenzamide-nitroargininate (V)

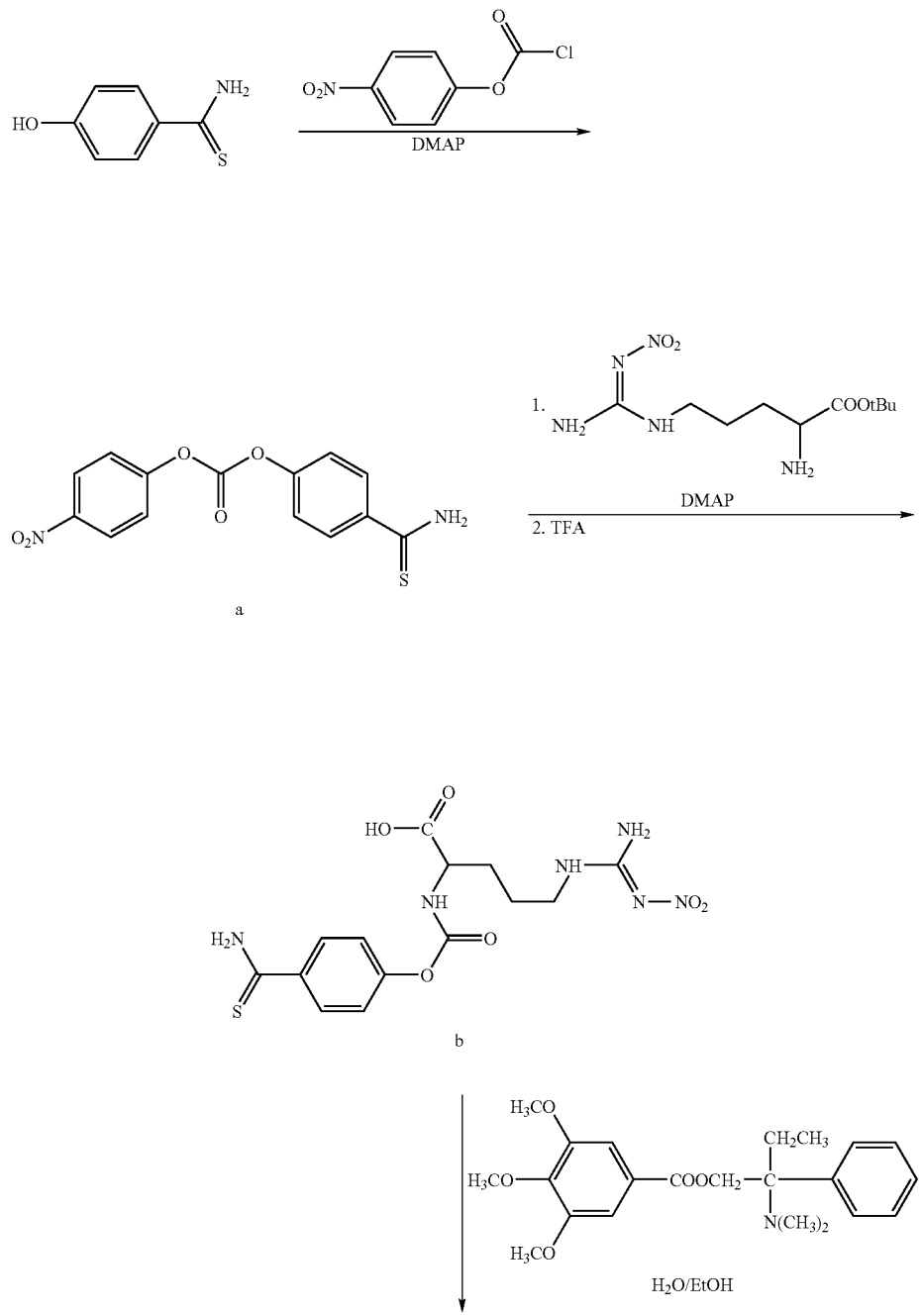

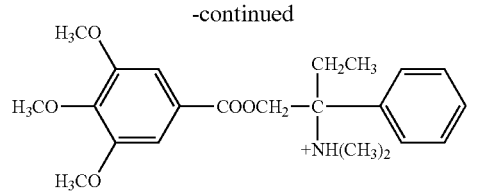

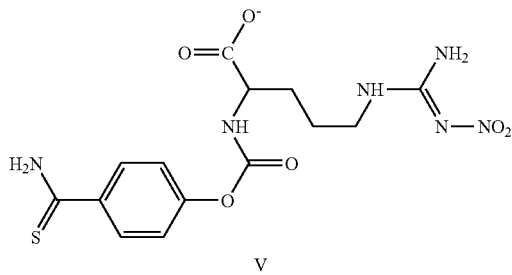

V

Synthesis of carbonic acid 4-nitro-phenyl ester 4-thiocarbamoyl-phenyl ester (a)

To a stirred suspension of p-hydroxythiobenzamide (1.04 mmol) in CH$_2$Cl$_2$ (10 ml) was added 4-dimethylaminopyridine (DMAP, 1.16 mmol) and 4-nitrophenyl chloroformate (1.15 mmol). The reaction mixture was stirred for 10 hr at room temperature. Thin layer chromatography indicated that the formation of the desired product completed. The solvent was removed and the residue was treated with diethyl ether; product a was recovered by filtration and used without further purification (yield 81%).

Synthesis of 5-nitroguanidino-2-(4-thiocarbamoyl-phenoxycarbonylamino)-pentanoic acid (b)

To the solution of a (1.04 mmol) in 50 mL of CH$_2$Cl$_2$ were added 4-dimethylaminopyridine (1.16 mmol) and H-Arg (NO$_2$)-OtBu (1.02 mmol) and the solution was stirred for 20 hr at room temperature. Then, the reaction mixture was diluted with CH$_2$Cl$_2$, washed with sat. NaHCO$_3$ and sat. NaCl, and dried over MgSO$_4$. The crude intermediate was treated with a solution of trifluoroacetic acid in dichloromethane (40% TFA in DCM). After 1 h the solvent was removed to obtain product b as a crude residue which was precipitated with diethyl ether; the obtained solid was dissolved in water and 1N NaOH was slowly added to obtain 5-nitroguanidino-2-(4-thiocarbamoyl-phenoxycarbonylamino)-pentanoic acid (b) as a white solid which was recovered by filtration.

Synthesis of trimebutine p-hydroxythiobenzamide-nitroargininate (V)

To a mixture of 5-nitroguanidino-2-(4-thiocarbamoyl-phenoxycarbonylamino)-pentanoic acid (b; 0.1 mole) and trimebutine (0.1 mole), water (200 mL) and ethyl alcohol (20 mL) have been added and the resulting suspension has been stirred at room temperature until clear. Then the solution has been frozen and lyophilized furnishing the desired salt (quantitative yield).

Example 6

Synthesis of N-desmethyltrimebutine nitroargininate (VI)

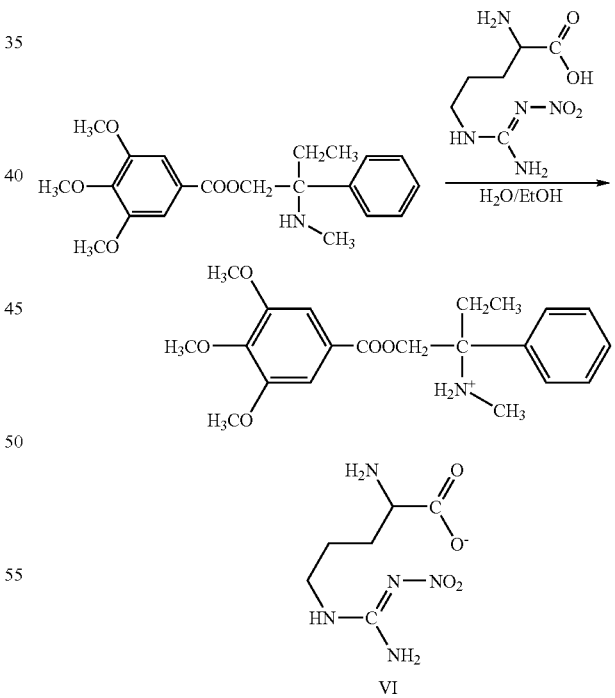

VI

To a mixture of H-Arg(NO$_2$)—OH (0.1 mol) and N-desmethyltrimebutine (0.1 mol), water (200 mL) and ethyl alcohol (20 mL) have been added and the resulting suspension has been stirred at room temperature until clear. Then the solution has been frozen and lyophilized furnishing the desired salt (quantitative yield).

¹H-NMR (400 MHz, DMSO-d₆): δ 0.72 (t, 3H), 1.45-1.75 (m, 4H), 1.80-1.90 (m, 2H), 2.07 (s, 3H), 2.90-3.40 (m, 2H), 3.75 (s, 9H), 3.95 (m, 1H), 4.64 (dd, 2H), 7.07 (s, 2H), 7.22 (t, 1H), 7.35 (t, 2H), 7.51 (d, 2H).

¹³C-NMR (400 MHz, DMSO-d₆): δ 9.07, 22.8, 26.4, 28.9, 29.1, 47.9, 56.4, 60.8, 64.4, 65.8, 107.3, 125.2, 127.4, 128.0, 128.5, 141.7, 142.5, 153.4, 158.3, 165.9, 170.2.

m.p. 78-80° C. (dec)

Synthesis of N-desmethyltrimebutine

The compound was synthesized following with slight modifications the procedure reported in literature (Martin, A., Figadère B., Saivin S., Houin G., Chomard J. M., Cahiez G. *Arzneim.-Forsch./Drug Res.* 2000 (50), 544).

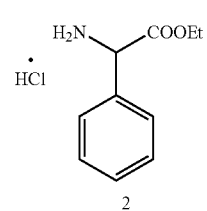

1

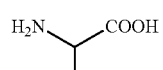

2

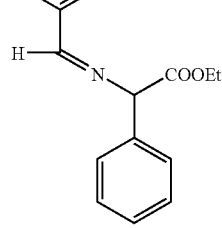

3

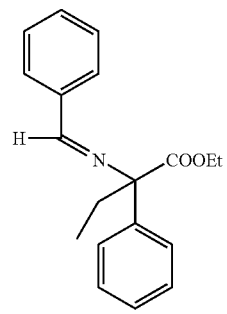

4

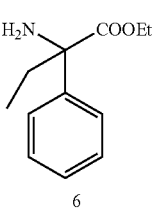

5    6

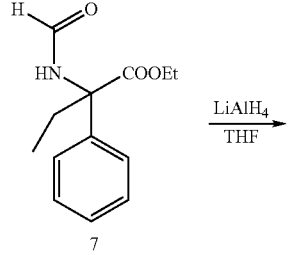

7

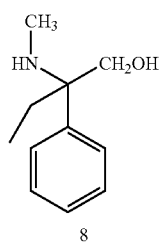

8

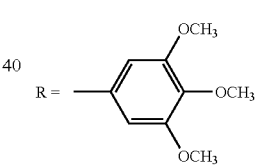

9

Phenylglycin ethylester hydrochloride (2)

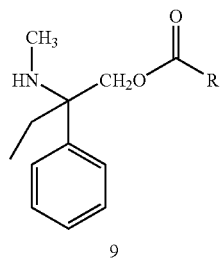

1    2

22 mL of SOCl₂ were added dropwise to a solution of 30 g of phenylglycin 1 (198.5 mmol) in 200 mL of anhydrous ethanol. A gentle reflux occurred spontaneously and it was maintained for 3 h. The reaction was allowed to cool to room temperature and was stirred overnight. The solvent was removed under vacuum to afford 41.8 g of 2 as a white powder (98% yield).

MS (ESI), m/e 179.8 (M⁺).

Ethyl N-(phenylmethylene)glycinate (3)

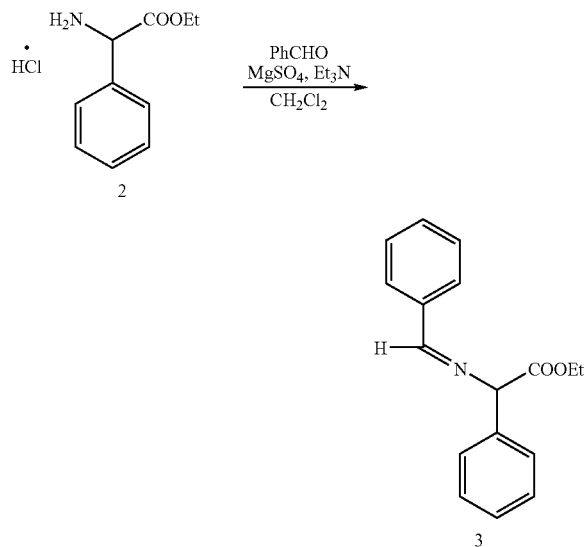

To a mixture of 10.6 g of ethyl phenylglycinate hydrochloride 2 (49.3 mmol), 100 mL of dichloromethane, 5 ml of benzaldehyde (49.2 mmol) and 30 g of magnesium sulfate (249.2 mmol) were added at room temperature, under a nitrogen atmosphere, 21.25 mL of triethylamine (152.46 mmol). After stirring for 17 h the heterogeneous reaction mixture was filtered through celite and the solid was washed with 100 mL of dichloromethane. The solvents were evaporated under reduced pressure and the viscous oil thus obtained was stirred with 80 mL of diethyl ether and 80 mL of water until dissolution. After decantation, the organic layer was dried over sodium sulphate and the solvent was evaporated under vacuum. The immine ester 3 (12.4 g, 94% yield) was obtained as a yellow pale oil.

MS (ESI), m/e 268.3 (M$^+$).

Ethyl 2-phenyl-2-(N-phenylmethylene)-butanoate (4)

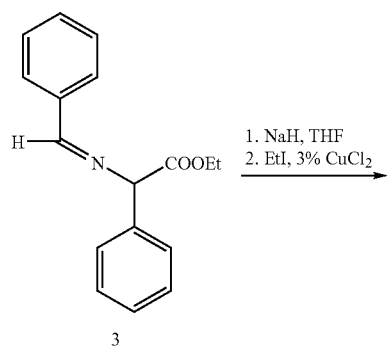

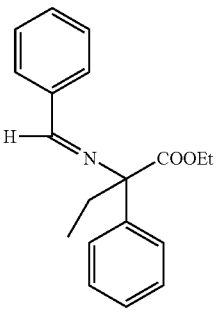

Under a nitrogen atmosphere, a solution of 12.39 g (46.4 mmol) of 3 in 64 mL of anhydrous THF was added dropwise, under stirring, to a mixture of 2.04 of sodium hydride (60% oil dispersion, 85 mmol), 192 mg of CuCl$_2$ and 128 mL of anhydrous THF. After 9 h at room temperature, 4.66 mL (57.7 mmol) of ethyl iodide were quickly added to the reaction mixture. Stirring was continued for 18 h and 0.86 mL of anhydrous ethanol were added cautiously to the reaction mixture. During the stirring the reaction color changed from yellow to red to orange and then to green. After concentration of the reaction mixture under vacuum, 95.8 mL of diethyl ether and 160 mL water were added and the resulting mixture was stirred for 10 minutes, then filtered through celite. After decantation the organic layer was washed three times with water and dried over sodium sulphate, then the diethyl ether was evaporated under reduced pressure to furnish 5.82 g of 4 (43% yield). The crude product, obtained as a yellow-orange oil, was pure enough to be used without further purification.

MS (ESI), m/e 296.1 (M$^+$).

Ethyl 2-amino-2-phenylbutanoate hydrochloride (5)

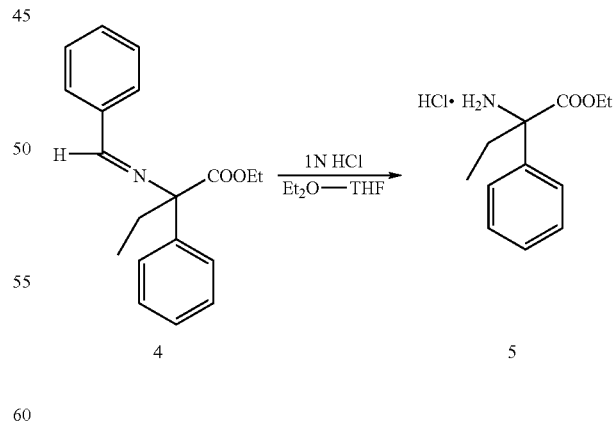

5.8 g of 4 (19.73 mmol), 17.6 mL of THF, 35.17 mL of diethyl ether, 44 mL of water and 2.64 mL of concentrated HCl were stirred at room temperature for 24 h. Solvents were removed from reaction mixture under vacuum and the resulting aqueous solution was washed twice with diethyl ether.

Water was then evaporated under reduced pressure to give 3.8 g of 5 as an orange oil (79% yield).

Ethyl 2-amino-2-phenylbutanoate (6)

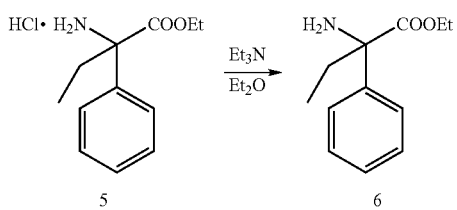

The crude product 5 was dissolved in 22 mL of anhydrous THF and 2.64 mL of triethyl amine were added. After stirring for 30 minutes, the mixture was filtered through celite and the solid washed with 100 mL of anhydrous diethyl ether. Concentration of the solvents using a rotary evaporator afforded 2.49 g of 6 as a blue oil (77% yield).
MS (ESI), m/e 208 (M$^+$).

Ethyl 2-Formylamino-2-phenylbutanoate (7)

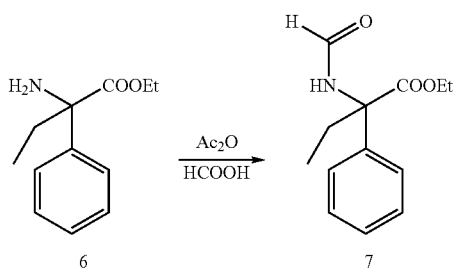

12.72 mL of formic acid then 25.38 mL of acetic anhydride were added dropwise, under stirring, to 2.49 g (12.03 mmol) of amine 6. After 15 h at room temperature, solvents were removed under reduced pressure to give 3.09 g of 7 as a green viscous oil (100% yield).
Rf=0.85 (CHCl$_3$/MeOH 9.5:0.5)
MS(ESI), m/e 236 (M$^+$).

2-Methylamino-2-phenylbutanol (8)

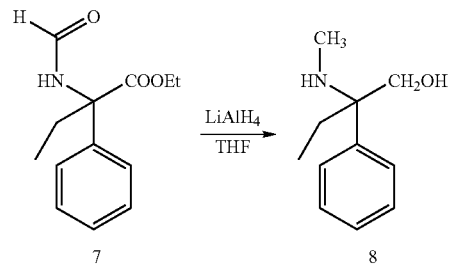

To a suspension of 900 mg (23.71 mmol) of lithium aluminum hydride (LiAlH$_4$) in 30 mL of anhydrous THF were added dropwise a solution of 3.09 g (13.15 mmol) of 7, previously prepared, in 18 mL of anhydrous THF. After 4 h under reflux, the reaction mixture was allowed to cool to room temperature and an additional amount of lithium aluminum hydride (900 mg) was introduced. Reflux was maintained for 4 h then an aqueous saturated solution of magnesium sulfate was slowly added at −10° C. under vigorous stirring until formation of a precipitate. The solid was filtered and washed several times with THF. The organic solvent was evaporated under reduced pressure until obtaining of an aqueous solution. The solution was added with 100 mL of diethyl ether and the organic layer was dried over sodium sulfate. Evaporation of the solvent afforded 1.84 g of 8 as a yellow oil. (78% yield).
MS(ESI), m/e 180.1 (M$^+$).

(2-Methylamino-2-phenylbutyl) 3,4,5-trimethoxybenzoate (N-desmethyltrimebutine (9)

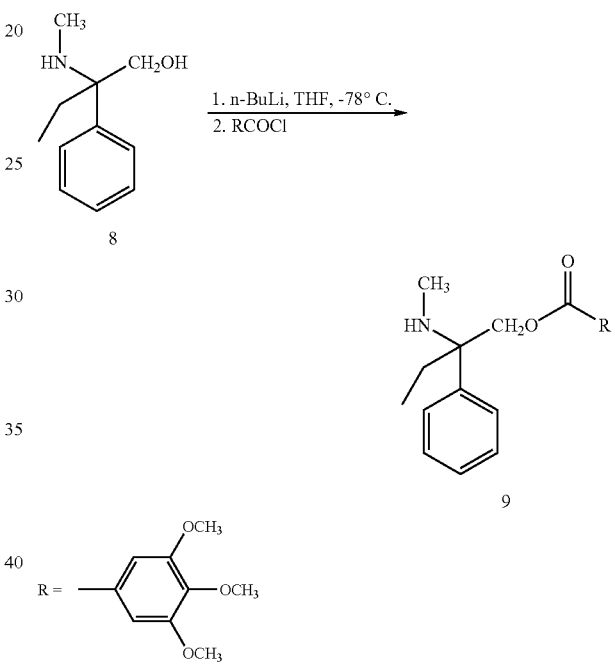

To a solution of 1.84 g of 8 (10.3 mmol) in 28 mL of anhydrous THF were added dropwise, at −78° C., 4.11 mL of n-BuLi (2.5 mol/L in hexanes). After 15 minutes, a solution of 2.31 g (10.01 mmol) of 3,4,5-trimethoxybenzoyl chloride in 15.8 mL of anhydrous THF was added. The reaction mixture was then allowed to warm to −30° C. (ca 1 h) and 19 mL of acetic acid were cautiously added. Solvents were removed under vacuum and 55 mL of diethyl ether and 55 mL of water were added to the previously obtained oil. After stirring until complete dissolution, the resulting mixture was then decanted and the aqueous layer alcalinized completely with solid Na$_2$CO$_3$ and re-extracted with diethyl ether. The organic layers were washed twice with a saturated aqueous solution of sodium carbonate and with brine and then dried over sodium sulphate. Diethyl ether was evaporated under vacuum and the ester 9 was purified by chromatography on silica gel column (ethyl acetate/n-hexane, 7:3) to give 1.4 g of pure N-desmethyltrimebutine 9 (49% yield) as a yellow pale oil. MS(ESI), m/e 374.1 (M$^+$).

$^1$H NMR (CDCl$_3$): δ 0.72 (t, 3H), 1.7 (s, 1H, NH), 1.75-1.9 (m, 2H), 2.6 (s, 3H), 3.76 (s, 6H), 3.80 (s, 3H), 4.50 (dd, 2H), 7.07-7.44 (m, 7H).

13C NMR (DMSO-d6): δ 7.4, 28.5, 28.6, 55.9, 60.1, 61.1, 66.3, 100.5, 126.5, 127.0, 129.3, 128.0, 142.0, 142.5, 152.7, 165.6.

Example 7

Synthesis of N-desmethyltrimebutine cysteinyl-nitroargininate (VII)

under reduced pressure to remove the solvent. The oily residue thus obtained was dissolved in ethyl acetate; the organic layer was washed with brine, dried on anhydrous MgSO4, filtered and the solvent evaporated. The crude intermediate a was treated with a solution of trifluoroacetic acid in dichloromethane (40% TFA in DCM). After 1 h the solvent was removed to obtain H-Cys-Arg(NO2)—OH.TFA as a crude residue which was precipitated with diethyl ether; the

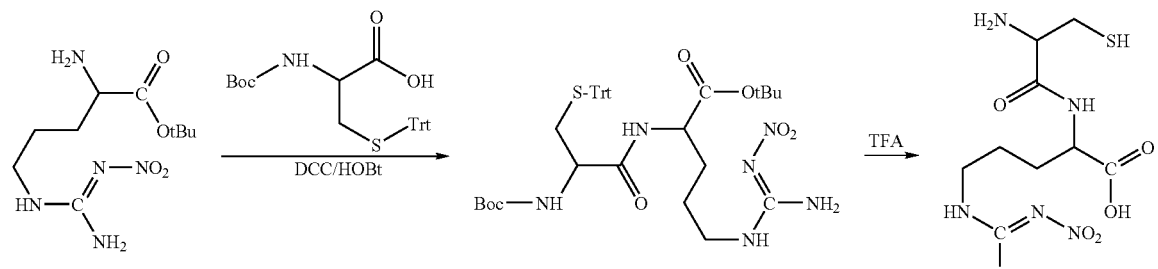

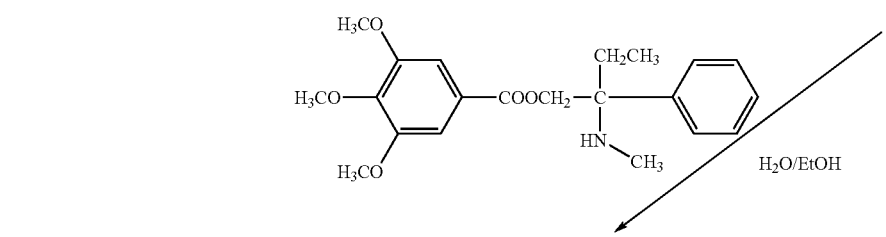

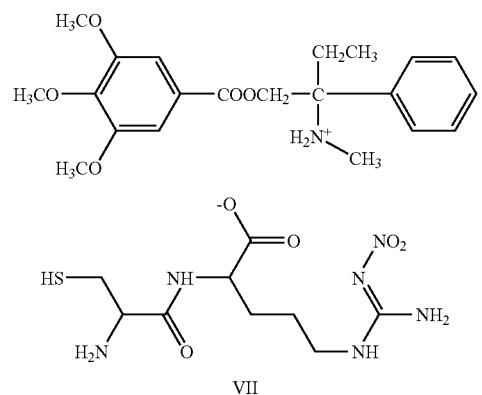

Synthesis of 2-(2-amino-3-mercapto-propionylamino)-5-nitroguanidino-pentanoic acid (b)

To a solution of Boc-Cys(Trt)-OH (3.0 mmol) in 50 mL of dimethylformamide, hydroxybenzotriazole (3.3 mmol) and DCC (3.3 mmol) were added with stirring at 0° C. for 1 h. To the reaction mixture, H-Arg(NO2)-OtBu (3.0 mmol) was added and stirred mechanically for 3 h at 0° C. and 24 h at room temperature. After filtration, the filtrate was evaporated obtained solid was dissolved in water and 1N NaOH was slowly added to obtain 2-(2-amino-3-mercapto-propionylamino)-5-nitroguanidino-pentanoic acid (b) as a white solid which was recovered by filtration.

Synthesis of N-desmethyltrimebutine cysteinyl-nitroargininate (VII)

To a mixture of 2-(2-amino-3-mercapto-propionylamino)-5-nitroguanidino-pentanoic acid (b; 0.1 mole) and N-desmethyltrimebutine (0.1 mole), water (200 mL) and ethyl alcohol (20 mL) have been added and the resulting suspension has been stirred at room temperature until clear. Then the solution has been frozen and lyophilized furnishing the desired salt (quantitative yield).

Example 8

Preparation of 3,4,5-trimethoxybenzoic acid 2-(methylamino)-2-phenylbutyl ester 4-thiocarbamoyl benzoate (N-desmethyltrimebutine thiocarbamoylbenzoate (VIII)

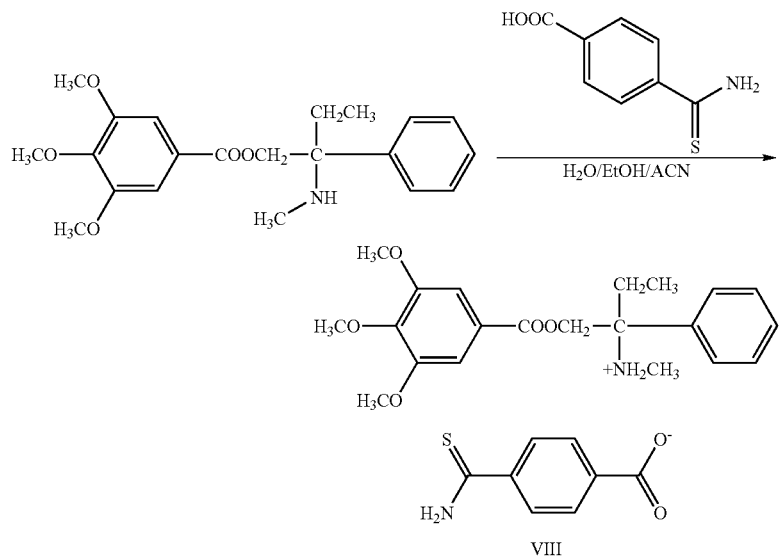

A mixture of 4-(thiocarbamoyl) benzoic acid (0.1 mol) and desmethyltrimebutine (0.1 mol) was dissolved in ethyl alcohol (20 mL) and acetonitrile (20 mL), then water (200 mL) has been added and the resulting suspension has been stirred at room temperature until clear. Then the solution has been frozen and lyophilized furnishing the desired salt (quantitative yield).

$^1$H-NMR (400 MHz, DMSO-$d_6$): δ 0.72 (t, 3H), 1.70-1.80 (m, 4H), 1.80-1.90 (m, 2H), 2.08 (s, 3H), 2.90-3.40 (m, 2H), 3.69 (s, 9H), 3.95 (m, 1H), 4.41 (dd, 2H), 7.07 (s, 2H), 7.22 (t, 1H), 7.33 (t, 2H), 7.52 (d, 2H) 7.93 (dd, 4H), 9.63 (bs, 1H, NH), 10.02 (bs, 1H, NH).

$^{13}$C-NMR (400 MHz, DMSO-$d_6$): δ 9.07, 28.7, 56.5, 60.5, 64.6, 65.8, 107.2, 125.5, 127.2, 128.2, 128.6, 129.5, 129.4, 132.5, 141.9, 142.4, 148.5, 153.5, 154.7, 165.7, 169.4, 172.5, 188.6.

mp 65-67° C. (dec.)

Example 9

Synthesis of N-desmethyltrimebutine ADT-nitroargininate (IX)

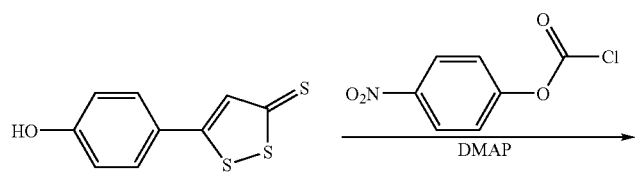

-continued
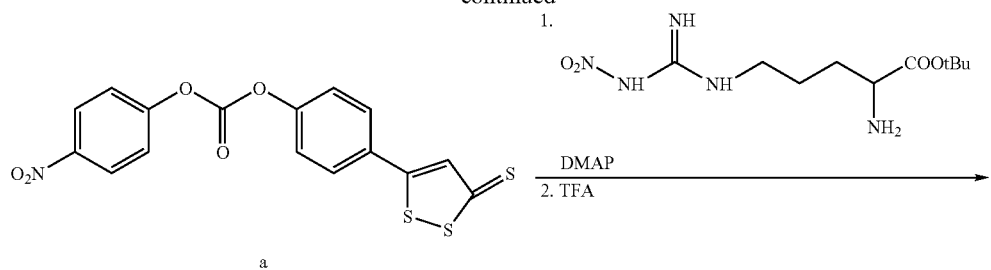
a
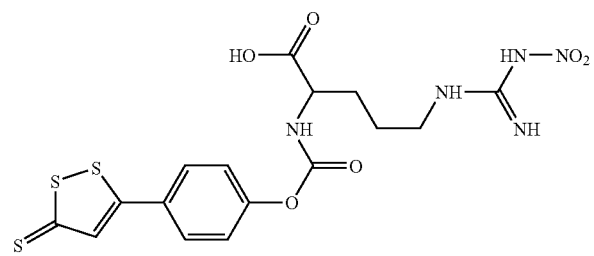
b
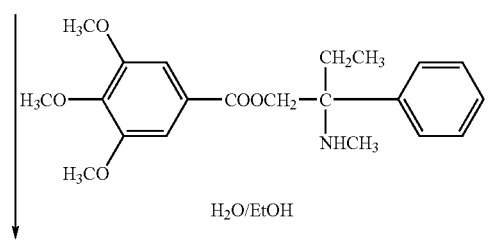
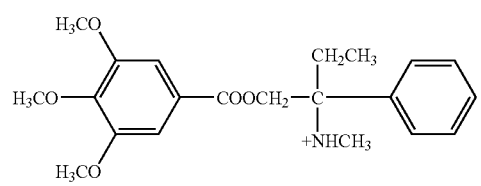
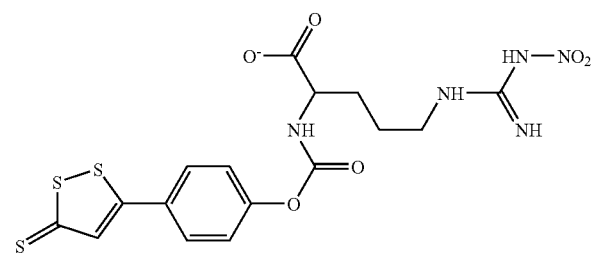
IX

Synthesis of carbonic acid 4-nitro-phenyl ester 4-(5-thioxo-5H-[1,2]dithiol-3-yl)-phenyl ester (a)

To a stirred suspension of ADT-OH (1.04 mmol) in CH$_2$Cl$_2$ (10 ml) was added 4-dimethylaminopyridine (DMAP, 1.16 mmol) and 4-nitrophenyl chloroformate (1.15 mmol). The reaction mixture was stirred for 10 hr at room temperature. Thin layer chromatography indicated that the formation of the desired product completed. The solvent was removed and the residue was treated with diethyl ether; product a was recovered by filtration and used without further purification (yield 81%).

Synthesis of 5-nitroguanidino-2-[4-(5-thioxo-5H-[1,2]dithiol-3-yl)-phenoxycarbonyl-amino]-pentanoic acid (b)

To the solution of a (1.04 mmol) in 50 mL of CH$_2$Cl$_2$ were added 4-dimethylaminopyridine (1.16 mmol) and H-Arg (NO$_2$)-OtBu (1.02 mmol) and the solution was stirred for 20 hr at room temperature. Then, the reaction mixture was diluted with CH$_2$Cl$_2$, washed with sat. NaHCO$_3$ and sat. NaCl, and dried over MgSO$_4$. The crude intermediate was treated with a solution of trifluoroacetic acid in dichloromethane (40% TFA in DCM). After 1 h the solvent was removed to obtain product b as a crude residue which was precipitated with diethyl ether; the obtained solid was dissolved in water and 1N NaOH was slowly added to obtain 5-nitroguanidino-2-[4-(5-thioxo-5H-[1,2]dithiol-3-yl)-phenoxycarbonyl-amino]-pentanoic acid (b) as a white solid which was recovered by filtration.

Synthesis of N-desmethyltrimebutine ADT-nitroargininate (IX)

To a mixture of 5-nitroguanidino-2-[4-(5-thioxo-5H-[1,2]dithiol-3-yl)-phenoxycarbonyl-amino]-pentanoic acid (b; 0.1 mol) and N-desmethyltrimebutine (0.1 mol), water (200 mL) and ethyl alcohol (20 mL) have been added and the resulting suspension has been stirred at room temperature until clear. Then the solution has been frozen and lyophilized furnishing the desired salt (quantitative yield).

Example 10

Synthesis of N-desmethyltrimebutine p-hydroxythiobenzamide nitro-argininate (X)

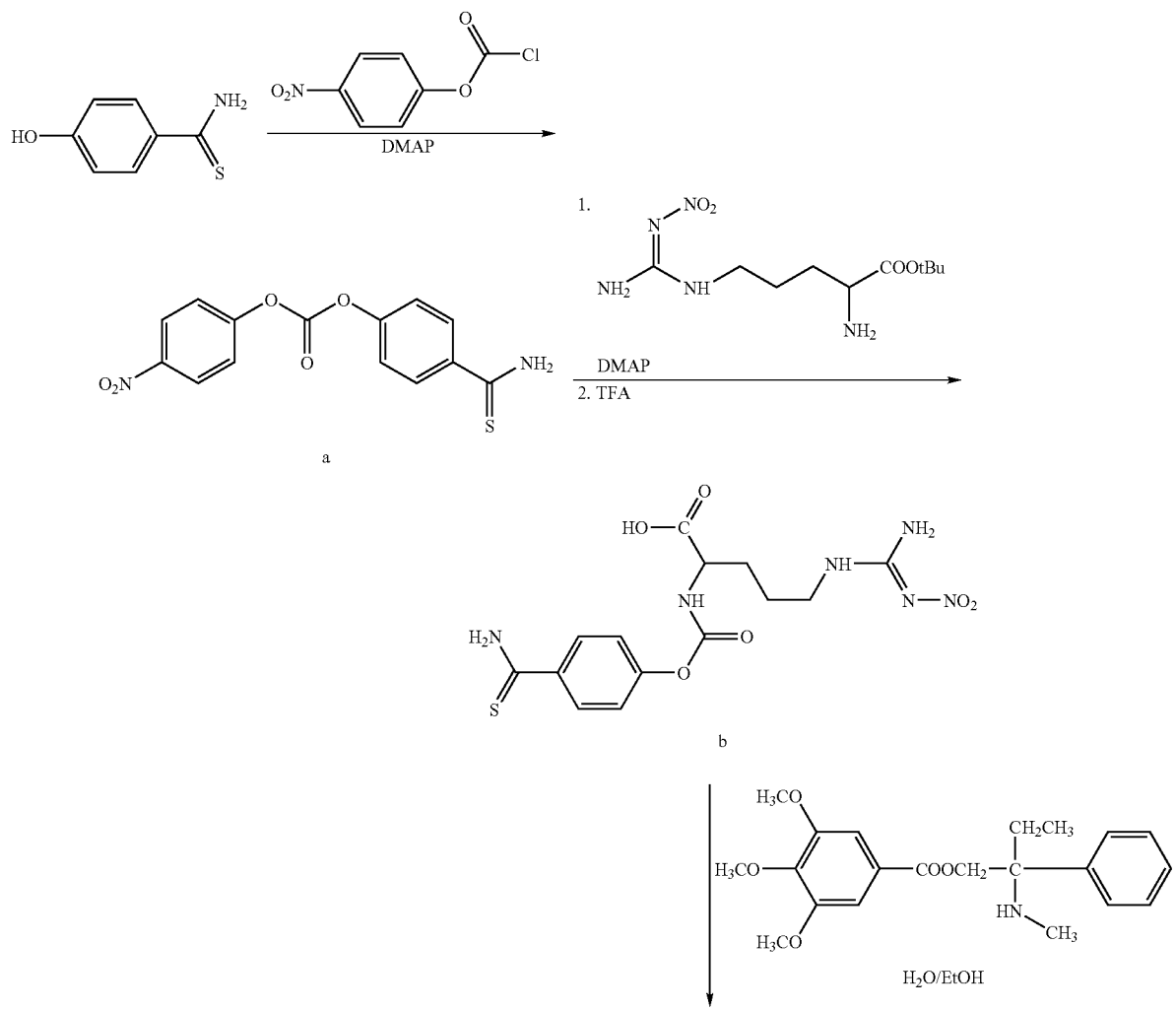

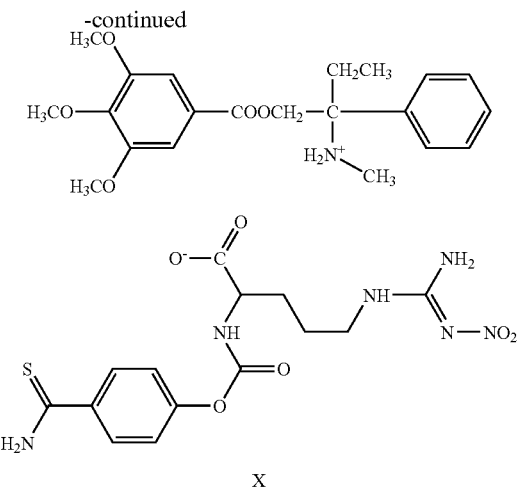

X

Synthesis of carbonic acid 4-nitro-phenyl ester 4-thiocarbamoyl-phenyl ester (a)

To a stirred suspension of p-hydroxythiobenzamide (1.04 mmol) in $CH_2Cl_2$ (10 ml) was added 4-dimethylaminopyridine (DMAP, 1.16 mmol) and 4-nitrophenyl chloroformate (1.15 mmol). The reaction mixture was stirred for 10 hr at room temperature. Thin layer chromatography indicated that the formation of the desired product completed. The solvent was removed and the residue was treated with diethyl ether; product a was recovered by filtration and used without further purification (yield 81%).

Synthesis of 5-nitroguanidino-2-(4-thiocarbamoyl-phenoxycarbonylamino)-pentanoic acid (b)

To the solution of a (1.04 mmol) in 50 mL of $CH_2Cl_2$ were added 4-dimethylaminopyridine (1.16 mmol) and H-Arg($NO_2$)-OtBu (1.02 mmol) and the solution was stirred for 20 hr at room temperature. Then, the reaction mixture was diluted with $CH_2Cl_2$, washed with sat. $NaHCO_3$ and sat. NaCl, and dried over $MgSO_4$. The crude intermediate was treated with a solution of trifluoroacetic acid in dichloromethane (40% TFA in DCM). After 1 h the solvent was removed to obtain product b as a crude residue which was precipitated with diethyl ether; the obtained solid was dissolved in water and 1N NaOH was slowly added to obtain 5-nitroguanidino-2-(4-thiocarbamoyl-phenoxycarbonylamino)-pentanoic acid (b) as a white solid which was recovered by filtration.

Synthesis of N-desmethyltrimebutine p-hydroxythiobenzamide-nitroargininate (X)

To a mixture of 5-nitroguanidino-2-(4-thiocarbamoyl-phenoxycarbonylamino)-pentanoic acid (b; 0.1 mole) and N-desmethyltrimebutine (0.1 mole), water (200 mL) and ethyl alcohol (20 mL) have been added and the resulting suspension has been stirred at room temperature until clear. Then the solution has been frozen and lyophilized furnishing the desired salt (quantitative yield).

Testing of Compounds

Example 11

Comparison of the Effects of Salt I, Trimebutine Nitroargininate, versus Trimebutine Alone and Nitroarginine Alone in a Rat Model of Visceral Pain Perception A rat model of visceral pain perception, a pre-clinical model of irritable bowel syndrome, was used in the following example. Rats (male, Wistar, 200-250 g, obtained from Charles River, Monza, Italy), were housed in plastic cages and maintained under controlled conditions with 12-hours light/dark cycle with lights on at 7.00 AM. Tap water and standard laboratory chow were freely available. Before experiments, rats were individually trained by spending 2-3 hours per day in a plexiglass cage for 2-3 days. It allowed them to adjust to a movement-restriction environment. Food was withheld for 12 hours before colorectal distension (CRD) recording were performed. Experiments were performed in awake rats and were conducted in a blind manner in that the observer was not aware of the identity of drug administered to each animal.

On the testing day, rats were sedated with ether inhalation and a 2 cm long latex balloon was inserted intrarectally 2 cm from the anal verge and fixed at the base of the tail. The balloon was connected via a double-barreled cannula to a pressure transducer to continuously monitoring the rectal pressure by a computer (PowerLab PC, A.D. Instruments, Milford, Mass., USA) and to a syringe for inflation/deflation of the balloon. The rats were then housed in a small cage (20×8×8 cm) on an elevated Plexiglas™ platform and allowed to wake up and adapt for 1 hour. After recovery from sedation, animals underwent the CRD procedure and behavioral responses were tested. The night before the experiments, the balloons were inflated and left overnight so the latex stretched and the balloons became compliant.

CRD of 20 seconds, performed every 5 minutes, was applied in increment of 0.4 ml starting from 0.4 ml up to 1.6 ml water. To achieve an accurate measurement of the colonic parameters and perception, the distensions were repeated twice for each intensity and data for each animal were averaged for analysis. Each animal underwent a double set of CRD. Twenty minutes after the first sequence of CRD (0.4 mL-1.6 ml water), drugs were administered intraperitoneally (i.p.) and a second set of CRD was performed. Behavioral responses during the first and the second set of CRD were assessed and compared.

Behavioral response to CRD was assessed by measuring the abdominal withdrawal reflex (AWR) using a semi-quantitative score (1). The AWR is an involuntary motor reflex similar to the visceromotor reflex, but it has the great advantage that, in contrast to the latter, it does not require abdominal surgery to implant recording electrodes and wires in the abdominal muscle wall which may cause additional sensitization (see Ness, T. J. and Gebhart, G. F. (1990) *Pain* 41:167-234, incorporated herein by reference).

Measurement of the AWR consisted of visual observation of the animal response to graded CRD by blinded observer and assignment of an AWR score according with the behavioral scale as previously described in Al-Chaer, E. D. et al. (2000) *Gastroenterology* 19: 1276-85, incorporated herein by reference, in which grade 0 corresponds to no behavioral response to CRD, grade 1 corresponds to brief head movement at the onset of the stimulus followed by immobility, grade 2 corresponds to a mild contraction of abdominal muscles although the rats does not lift the abdomen off the platform, grade 3 corresponds to a strong contraction of the abdominal muscles with the lifting of the abdomen off the platform, and grade 4 corresponds to a severe contraction of the abdominal muscle manifested by body arching and the lifting of the abdomen and of the pelvic structures and scrotum.

The effects of trimebutine maleate, nitroarginine and trimebutine nitroargininate on colonic compliance and sensitivity were determined using a total of 15 fasting rats. To investigate whether the administration of trimebutine maleate, nitroarginine and trimebutine nitroargininate could reduce pain induced by CRD, after the first sequence of CRD (vehicle-treated), 5 rats were treated with trimebutine maleate at a dose of 10 mg/kg i.p., nitroarginine at a dose of 6 mg/kg or trimebutine nitroargininate at the dose of 16 mg/kg i.p., after which a second set of CRD was repeated. Results from these experiments are shown in FIGS. 1(*a*), 2(*a*) and 3(*a*).

To determine the effect of trimebutine maleate, nitroarginine and trimebutine nitroargininate on colonic smooth muscle, the compliance of the colo-rectum during CRD was obtained from intracolo-rectal volume and pressure and expressed as mL/mmHg. These results are shown in FIGS. 1(*b*), 2(*b*) and 3(*b*).

Figure 4A:
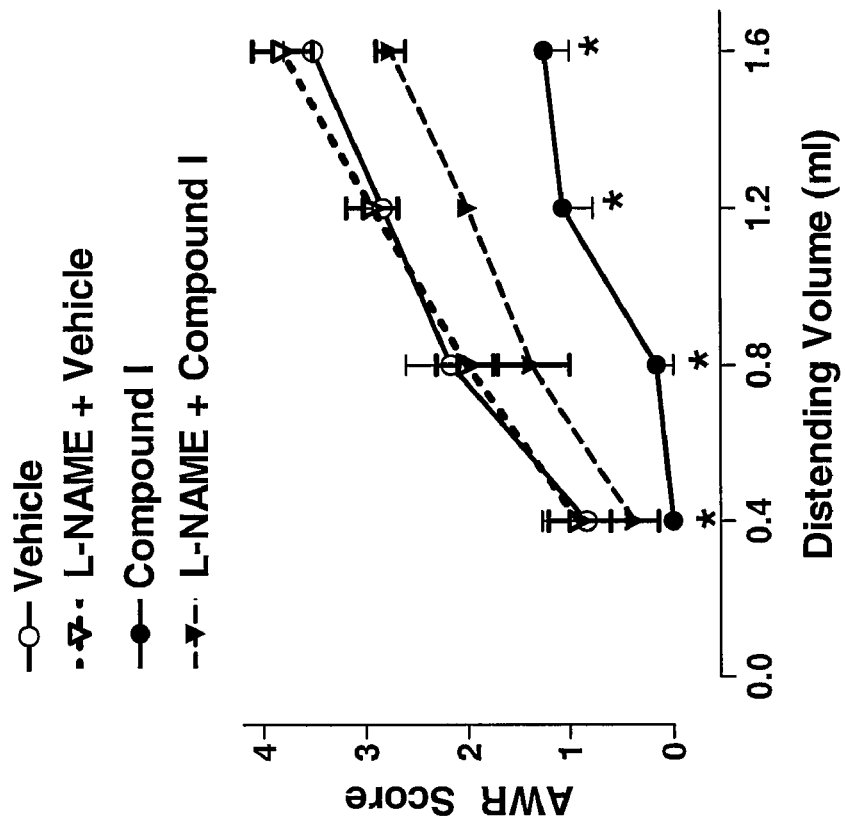
FIG. 4(a) shows the perception score (AWR Score) in a rat model of visceral pain perception using vehicle or trimebutine nitroargininate (salt I), with or without pretreatment with L-NAME.
Figure 4B:
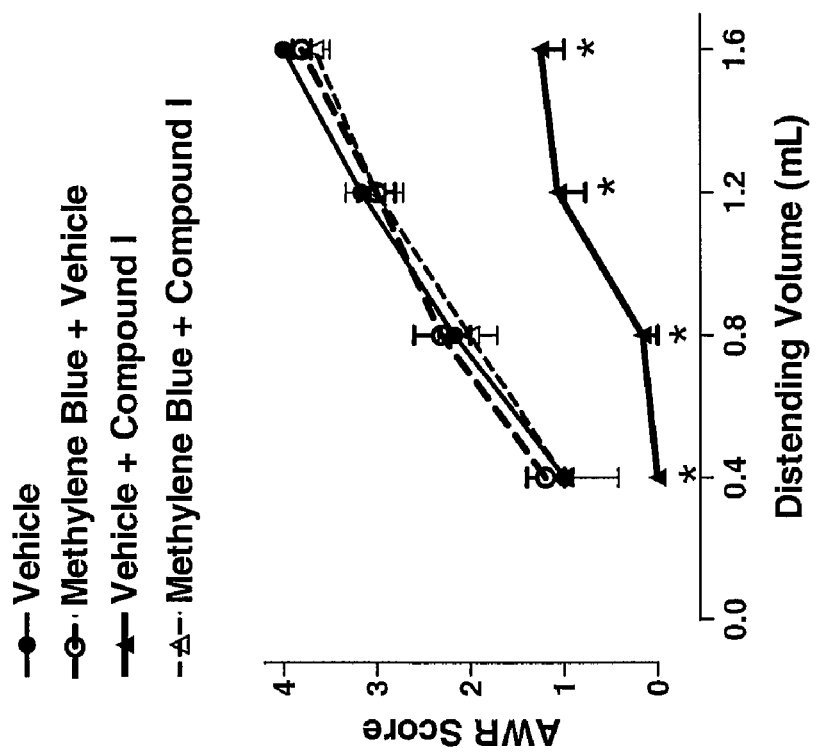
FIG. 4(b) shows the perception score (AWR Score) in a rat model of visceral pain perception using vehicle or trimebutine nitroargininate (salt I), with or without pretreatment with methylene blue.

To determine the role of NO in the visceral analgesic effects of trimebutine nitroargininate, experiments were performed in which rats were pretreated 10 min before administration of trimebutine nitroargininate (16 mg/kg i.p.) or vehicle with methylene blue (1 mg/kg i.p.), L-NAME (25 mg/kg i.v.) or vehicle. The results are shown in FIGS. 4(*a*) and 4(*b*).

All data are presented as the mean±SEM, with sample sizes of 5 rats/group; statistical comparison of data was performed by the Student's paired t-test. An associated probability (p value) of less that 5% was considered significant, as indicated by an asterisk.

FIGS. 1(*a*), 2(*a*) and 3(*a*) show that trimebutine nitroargininate is more effective than either trimebutine maleate or nitroarginine in reducing visceral pain in response to colorectal distension. However, none of the compounds were particularly effective in reducing intrarectal pressure, as shown in FIGS. 1(*b*), 2(*b*) and 3(*b*). FIGS. 4(*a*) and 4(*b*) show that the visceral analgesic effects of trimebutine nitroargininate are largely abolished by pretreatment with an inhibitor of nitric oxide synthase (L-NAME) or with an inhibitor of soluble guanylate cyclase (methylene blue). These results suggest that release of nitric oxide from trimebutine nitroargininate, and stimulation of soluble guanylate cyclase, contribute significantly to the visceral analgesic effects of this compound.

Thus, trimebutine nitroargininate is useful in treating abdominal pain associated with various inflammatory conditions of the alimentary tract, as well as functional gastrointestinal disorders such as irritable bowel syndrome, dyspepsia, etc., that are characterized by increased visceral nociception (with or without accompanying inflammation).

Example 12

Comparison of the Effects of Salt III, Trimebutine Thiocarbamoylbenzoate, versus Trimebutine Alone and Thiocarbamoylbenzoate Alone, in a Rat Model of Visceral Pain Perception Experiments were carried out as described in Example 11, except that groups of 5 rats each were treated with vehicle, trimebutine maleate (10 mg/kg), or with equimolar doses of trimebutine thiocarbamoylbenzoate (salt III) or thiocarbamoylbenzoate alone.

Figure 5A:
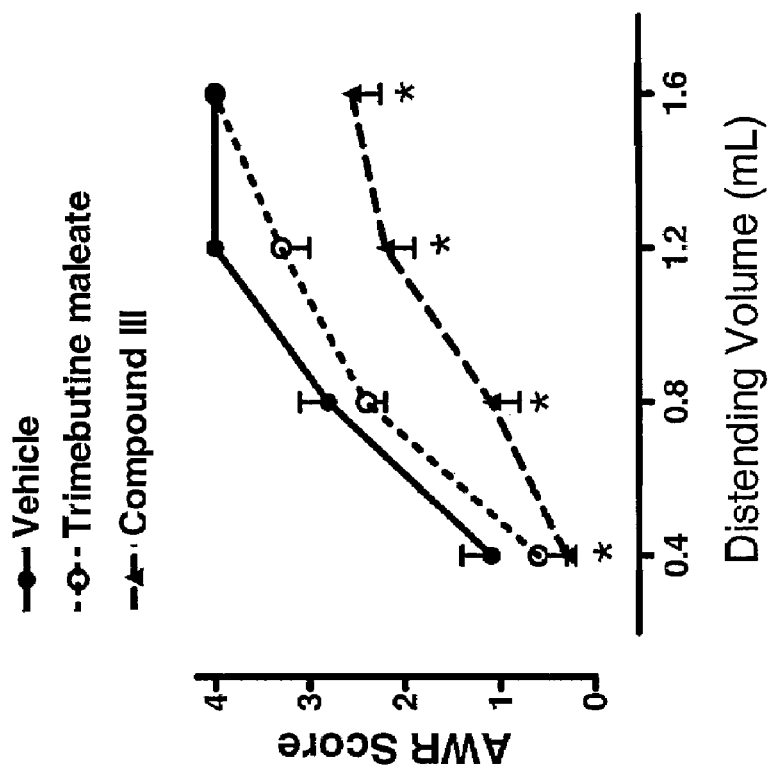
FIG. 5(a) shows the perception score (AWR Score) in a rat model of visceral pain perception using vehicle, trimebutine maleate and trimebutine thiocarbamoylbenzoate (salt III).
Figure 5B:
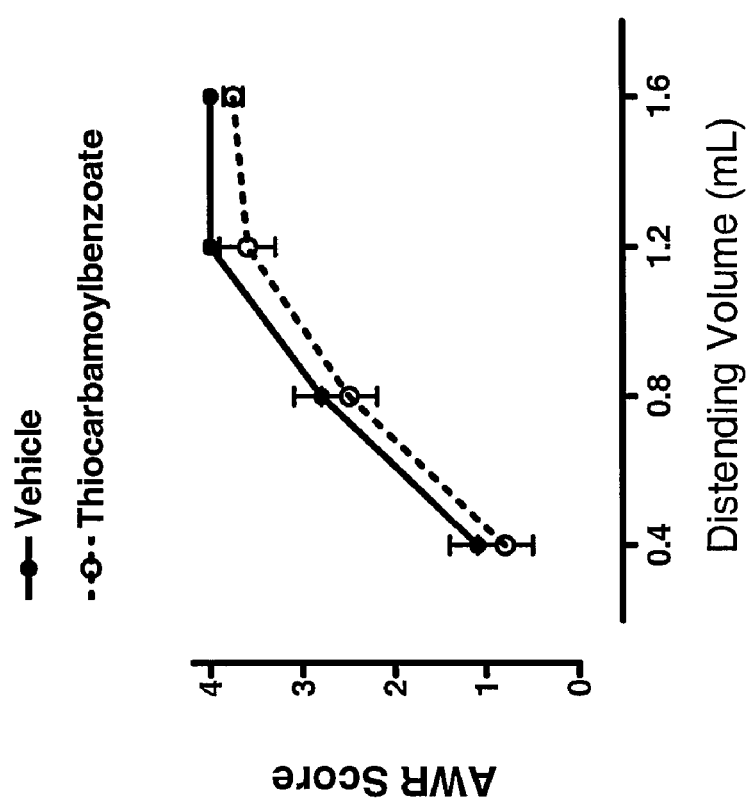
FIG. 5(b) shows the perception score (AWR Score) in a rat model of visceral pain perception using vehicle and thiocarbamoylbenzoate (TBZ) alone.

FIGS. 5(*a*) and 5(*b*) show that trimebutine thiocarbamoylbenzoate is more effective than either trimebutine maleate or thiocarbamoylbenzoate in reducing visceral pain in response to colorectal distension.

Thus, trimebutine thiocarbamoylbenzoate is useful in treating abdominal pain associated with various inflammatory conditions of the alimentary tract, as well as functional gastrointestinal disorders such as irritable bowel syndrome, dyspepsia, etc., that are characterized by increased visceral nociception (with or without accompanying inflammation).

Example 13

Figure 6:
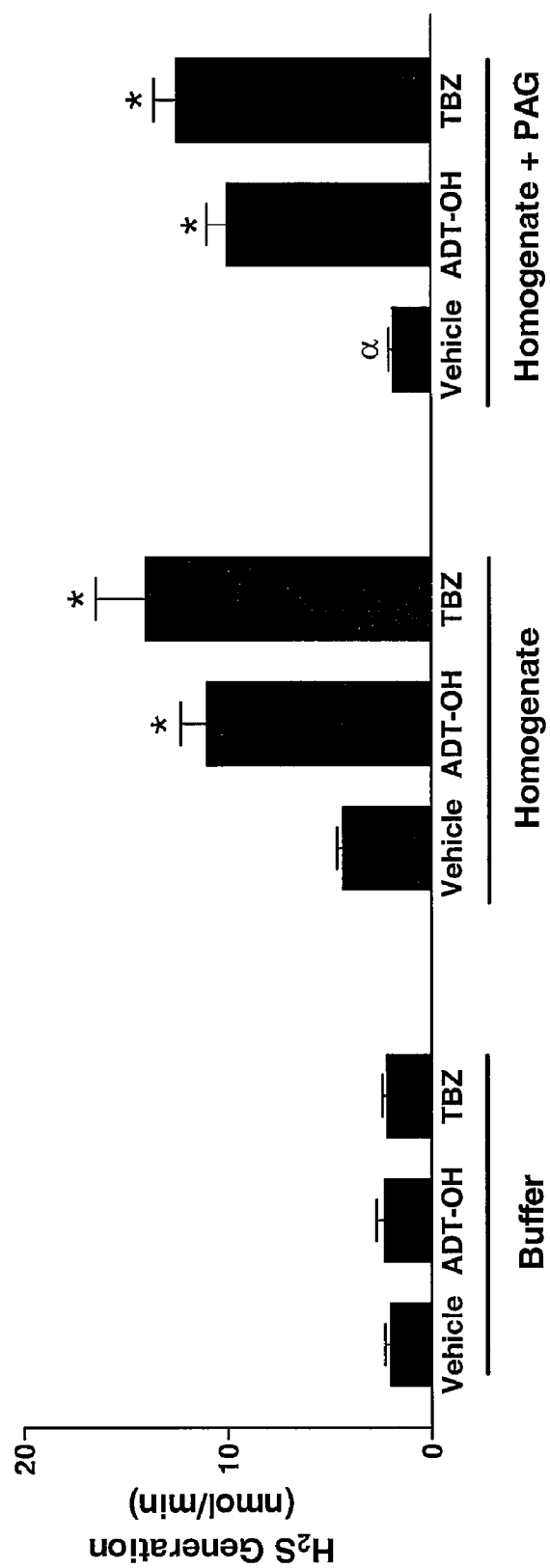
FIG. 6 is a bar graph showing $H_2S$ generation of 4-(thiocarbamoyl) benzoic acid (TBZ) and 5-(4-amino-phenyl)-[1,2]dithiole-3-thione (ADT-OH).

Generation of $H_2S$ by 4-(thiocarbamoyl) benzoic acid and 5-(4-Amino-phenyl)-[1,2]dithiole-3-thione Two compounds were tested, 5-(4-Amino-phenyl)-[1,2] dithiole-3-thione (ADT-OH) and 4-(thiocarbamoyl) benzoic acid (TBZ) for $H_2S$ generation under three different conditions for $H_2S$ generation. In particular, concentrations of $H_2S$ generated within 1 hour from 1 mM concentrations ADT-OH and TBZ were measured. $H_2S$ release was tested under three conditions: (i) when the compound was in buffer, (ii) when the compound was in a liver homogenate, and (iii) when the compound was in the liver homogenate together with an inhibitor of $H_2S$ synthesis, which blocks the activity of the enzyme an inhibitor of cystathionine-γ-lyase (PAG=DL-propargylglycine; 2 mM). Results are shown in FIG. 6. Asterisk (*) indicates a significant (p<0.05) increase versus corresponding vehicle-treated group. The alpha (a) represents a significant decrease in $H_2S$ synthesis as a result of incubation in the presence of PAG.

We claim:
1. A compound of the general formula:

A⁺.X⁻ where:
A is

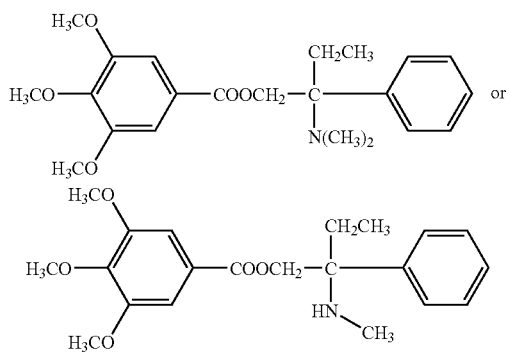

and their corresponding stereoisomers; and
X is selected from the group consisting of:

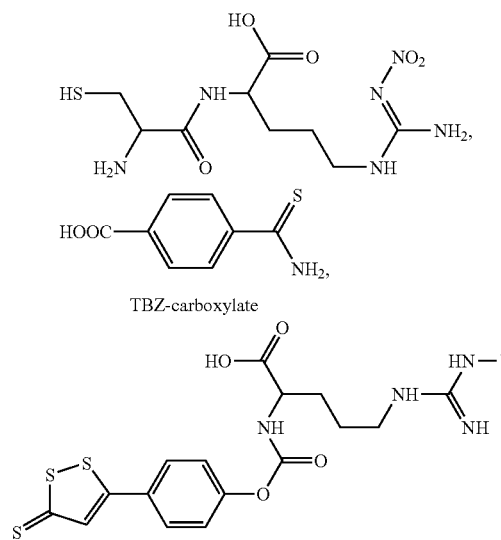

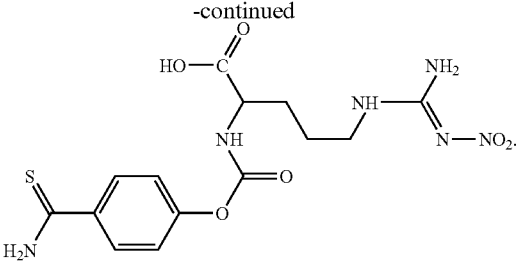

2. The compound according to claim 1 where the compound is trimebutine cysteinyl-nitroargminate.

3. The compound according to claim 1 where the compound is trimebutine thiocarbamoyl benzoate.

4. The compound according to claim 1 where the compound is trimebutine 5-phenyl-1,2-dithione-3-thione-nitrocargininate.

5. The compound according to claim 1 where the compound is trimebutine p-hydroxythiobenzamide-nitroargininate.

6. The compound according to claim 1 where the compound is N-desmethyltrimebutine cysteinyl-nitroargininate.

7. The compound according to claim 1 wherein the compound is N-desmethyltrimebutine thiocarbamoylbenzoate.

8. The compound according to claim 1 wherein the compound is N-desmethyltrimebutine 5-phenyl-1,2-dithione-3-thione-nitroargininate.

9. The compound according to claim 1 wherein the compound is N-desmethyltrimebutine p-hydroxythiobenzamide-nitroargininate.

10. A compound having the general formula nitroarginine-R, wherein R is selected from the group consisting of 5-p-hydroxyphenyl-1,2-dithione-3-thione, cysteine, and 4-(thiocarbamoyl)benzoic acid, for the preparation of salts of trimebutine and N-monodesmethyl trimebutine.

* * * * *